(12) United States Patent
Bowlin et al.

(10) Patent No.: US 7,374,774 B2
(45) Date of Patent: May 20, 2008

(54) ELECTROPROCESSED MATERIAL MADE BY SIMULTANEOUSLY ELECTROPROCESSING A NATURAL PROTEIN POLYMER AND TWO SYNTHETIC POLYMERS

(75) Inventors: Gary L. Bowlin, Mechanicsville, VA (US); Gary E. Wnek, Midlothian, VA (US); David G. Simpson, Mechanicsville, VA (US)

(73) Assignee: Virginia Commonwealth University Intellectual Property Foundation, Richmond, VA (US)

( * ) Notice: Subject to any disclaimer, the term of this patent is extended or adjusted under 35 U.S.C. 154(b) by 0 days.

(21) Appl. No.: 10/668,085

(22) Filed: Sep. 22, 2003

(65) Prior Publication Data

US 2004/0058887 A1    Mar. 25, 2004

Related U.S. Application Data

(63) Continuation of application No. 09/982,515, filed on Oct. 18, 2001, now abandoned, which is a continuation-in-part of application No. 09/946,158, filed on Sep. 4, 2001, now abandoned, which is a continuation-in-part of application No. 09/654,517, filed on Sep. 1, 2000, now abandoned, said application No. 09/982,515 is a continuation-in-part of application No. 09/714,255, filed on Nov. 17, 2000, now abandoned, which is a continuation-in-part of application No. 09/512,081, filed on Feb. 24, 2000, now abandoned, which is a continuation-in-part of application No. 09/386,273, filed on Aug. 31, 1999, now Pat. No. 6,592,623, said application No. 09/982,515 is a continuation-in-part of application No. 09/512,081, filed on Feb. 24, 2000, now abandoned, which is a continuation-in-part of application No. 09/386,273, filed on Aug. 31, 1999, now Pat. No. 6,592,623, said application No. 09/982,515 is a continuation-in-part of application No. 09/386,273, filed on Aug. 31, 1999, now Pat. No. 6,592,623.

(60) Provisional application No. 60/270,118, filed on Feb. 22, 2001, provisional application No. 60/241,008, filed on Oct. 18, 2000.

(51) Int. Cl.
*A61F 2/02* (2006.01)
*A61K 9/70* (2006.01)
*A61K 38/39* (2006.01)
*C07K 14/78* (2006.01)

(52) U.S. Cl. .................. 424/423; 424/443; 424/485; 424/486; 530/356; 514/12; 514/801

(58) Field of Classification Search ............... 424/422, 424/423, 443, 485, 486; 530/353, 356; 428/311.11; 514/12, 801
See application file for complete search history.

(56) References Cited

U.S. PATENT DOCUMENTS

| | | | |
|---|---|---|---|
| 1,975,504 A | 10/1934 | Formhals | |
| 3,892,648 A | 7/1975 | Phillips et al. | |
| 4,043,331 A | * 8/1977 | Martin et al. | ............... 602/45 |
| 4,044,404 A | 8/1977 | Martin et al. | |
| 4,294,677 A | 10/1981 | Sakagami et al. | |
| 4,552,707 A | 11/1985 | How | |
| 4,565,736 A | 1/1986 | Stein et al. | |
| 4,657,793 A | 4/1987 | Fisher | |
| 4,738,740 A | 4/1988 | Pinchuk et al. | |
| 5,171,505 A | 12/1992 | Lock | |
| 5,252,285 A | 10/1993 | Lock | |
| 5,256,418 A | 10/1993 | Kemp et al. | |
| 5,292,362 A | 3/1994 | Bass et al. | |
| 5,332,475 A | * 7/1994 | Mechanic | ............. 204/157.68 |
| 5,580,859 A | 12/1996 | Felgner et al. | |
| 5,655,517 A | 8/1997 | Coffee | |
| 5,693,085 A | 12/1997 | Buirge et al. | |
| 5,723,324 A | 3/1998 | Bowlin et al. | |
| 5,813,614 A | 9/1998 | Coffee | |
| 5,902,741 A | 5/1999 | Purchio et al. | |
| 5,906,934 A | 5/1999 | Grande et al. | |
| 5,908,777 A | 6/1999 | Lee et al. | |
| 5,912,177 A | 6/1999 | Turner et al. | |

| | | |
|---|---|---|
| 5,915,377 A | 6/1999 | Coffee |
| 5,948,654 A | 9/1999 | Tranquillo et al. |
| 6,057,137 A | 5/2000 | Tranquillo et al. |
| 6,068,199 A | 5/2000 | Coffee |
| 6,093,557 A | 7/2000 | Pui et al. |
| 6,096,309 A | 8/2000 | Prior et al. |
| 6,100,026 A | 8/2000 | Nova et al. |
| 6,103,255 A | 8/2000 | Levene et al. |
| 6,105,571 A | 8/2000 | Coffee |
| 6,105,877 A | 8/2000 | Coffee |
| 6,106,913 A | 8/2000 | Scardino et al. |
| 6,110,484 A | 8/2000 | Sierra |
| 6,110,590 A | 8/2000 | Zarkoob et al. |
| 6,117,296 A | 9/2000 | Thomson |
| 6,121,042 A | 9/2000 | Peterson et al. |
| 6,146,892 A | 11/2000 | Ma et al. |
| 6,179,872 B1 | 1/2001 | Bell et al. |
| 6,180,605 B1 | 1/2001 | Chen et al. |
| 6,180,606 B1 | 1/2001 | Chen et al. |
| 6,190,893 B1 | 2/2001 | Shastri et al. |
| 6,197,575 B1 | 3/2001 | Griffith et al. |
| 6,245,345 B1 | 6/2001 | Swanbom et al. |
| 6,252,129 B1 | 6/2001 | Coffee |
| 6,254,627 B1 | 7/2001 | Freidberg |
| 6,265,333 B1 | 7/2001 | Dzenis et al. |
| 6,306,424 B1 | 10/2001 | Vyakarnam et al. |
| 6,308,509 B1 | 10/2001 | Scardino et al. |
| 6,309,669 B1 | 10/2001 | Setterstrom et al. |
| 6,318,640 B1 | 11/2001 | Coffee |
| 6,386,195 B1 | 5/2002 | Coffee |
| 6,399,362 B1 | 6/2002 | Pui et al. |
| 2001/0003148 A1 | 6/2001 | Coffee |
| 2002/0084178 A1 | 7/2002 | Dubson et al. |
| 2002/0089094 A1 | 7/2002 | Kleinmeyer et al. |
| 2002/0091437 A1 | 7/2002 | Tseng et al. |
| 2002/0172705 A1* | 11/2002 | Murphy et al. ............. 424/422 |
| 2004/0072756 A1 | 4/2004 | Wilkie et al. |

FOREIGN PATENT DOCUMENTS

| | | |
|---|---|---|
| EP | 0234841 A2 | 9/1987 |
| EP | 0234842 A2 | 9/1987 |
| EP | 0234842 B1 | 9/1987 |
| EP | 0250102 A2 | 12/1987 |
| EP | 0250164 A2 | 12/1987 |
| EP | 0250164 B1 | 1/1991 |
| EP | RU2031661 C1 | 3/1995 |
| EP | 1 006 950 | 6/2000 |
| GB | 1377022 | 12/1974 |
| GB | 2360789 A | 10/2001 |
| RU | 2031661 | 3/1995 |
| RU | 2034534 C1 | 5/1995 |
| WO | WO 94/13266 A1 | 6/1994 |
| WO | WO 95/26235 A1 | 10/1995 |
| WO | WO 9803267 A | 1/1998 |
| WO | WO 9803267 A1 * | 1/1998 |
| WO | WO 99/66964 | 12/1999 |
| WO | WO 00/67694 A1 | 11/2000 |
| WO | WO 00/72857 A1 | 12/2000 |
| WO | WO 02/13786 A2 | 2/2001 |
| WO | WO-01/015754 | 3/2001 |
| WO | WO 01/26610 A1 | 4/2001 |
| WO | WO 01/26702 A2 | 4/2001 |
| WO | WO 01/27365 A1 | 4/2001 |
| WO | WO 01/51690 A1 | 7/2001 |
| WO | WO 01/74431 A2 | 10/2001 |
| WO | WO-01/080921 | 11/2001 |
| WO | WO 02/00149 A1 | 1/2002 |
| WO | WO 2004/028404 | 4/2004 |
| WO | WO 2004/028547 | 4/2004 |

OTHER PUBLICATIONS

Doshi et al., "Electrospinning process and applications of electrospun fibers," J Electrostatics 35:151-160, 1995).*

Abstract of FR1494094, Polymer-bonded leather-like sheet material, F. Andrieu, Sep. 8, 1967, Derwent.

Abstract of JP 08-035193, Preparation of sheet of nonwoven fabric of collagen fibre—by injecting acidic solution of soluble collagen through spinning dyes into aq. conc. solution of salt, cutting obtd. fibre and paper making, Mitsubishi Rayon Co. Ltd., Feb. 6, 1996, Derwent.

Abstract of RU2031661, Nauchno-proizvodstvennoe predprijatie "Ehkomedservis," Institut Khirurgii im.A.V.Vishnevskogo RAMN, Derwent, XP 00204663.

Abstract of RU 2034534, Kirichenko, et al. Derwent World Patents Inc., Dialog File No. 351 Accession No. 10521633.

Agrawal, C.M. et al., "Technique to Control pH in Vicinity of Biodegrading PLA-PGA Implants", J. Biomed. Mater Res., 1997, pp. 105-114, vol. 38.

Akins, R.E. et al., "Neonatal Rat Heart Cells Cultured in Simulated Microgravity",In Vitro Cell. Dev. Biol.—Animal, 1997, pp. 337-343, vol. 33.

Amsden et al., "An examination of factors affecting the size, distribution and release characteristics of polymer microbeads made using electrostatics", Journal of Controlled Release, 1997, pp. 183-196, vol. 43.

Baker, T.L. et al., "Three-Dimensional Culture of Bovine Chondrocytes in Rotating-Wall Vessels", In Vitro Cell. Dev. Biol.—Animal, 1997, pp. 358-365, vol. 33.

Boland et al., "Tailoring a Poly (Glycolic Acid) Tissue Engineering Scaffold by Utilizing Electrostatic Processing," Abstract of Presentation at the 4th International Symposium on Frontiers in Biomedical Polymers, Williamsburg, VA, May 16, 2001.

Boland et al., "Electrospinning of Tissue Engineering Scaffolds," Paper Presented at American Chemical Society Div. Of Polymeric Materials: Science and Engineering, Presented Aug. 26, 2001, Chicago, IL, Publication approximately Jul. 2001.

Bowlin et al., "Electrospinning of Biomaterials," Abstract for Presentation at the Second Conference on the Development of Technology in Medicine for Virginia, at the University of Virginia, Presented Nov. 2, 1999.

Bowlin et al., "Electric Field-Mediated Processing of Biomaterials: Toward Nanostructured Biomimetic Systems," Abstract of Presentation at SPIE Annual Meeting, Newport Beach, CA, presented Mar. 8, 2001.

Bowlin, G., "The New 'Spin' on Tissue Engineering Scaffolds," Abstract for Keynote Address at the 4th International Symposium on frontiers in Biomedical Polymers, Williamsburg, VA, Presented May 17, 2001.

Bowlin et al., "Electrospinning of Biomaterials," Paper for Presentation at Fiber Society Spring 2001 Meeting, Raleigh, NC, Presented May 23, 2001.

Bowlin, G., "Biomimicking Small Caliber Vascular Construct Engineering," Abstract for Presentation at 2001 Whitaker Foundation Biomedical Engineering Conference, La Jolla, CA, Presented Aug. 9, 2001.

Buchko, C.J. et al., "Processing and Microstructural Characterization of Porous Biocompatible Protein Polymer Thin Films", Polymer, 1999, pp. 7397-7407, vol. 40.

Cavallaro, J.F. et al., "Collagen Fabrics as Biomaterials", Biotechnology and Bioengineering, 1994, pp. 781-791, vol. 43.

Chen, Da-Ren et al., "Experimental Investigation of Scaling Laws for Electrospraying: Dielectric Constant Effect", Aerosol Science and Technology, 1997, pp. 367-380, vol. 27.

Deitzel, J.M. et al., "Generation of Polymer Nanofibers Through Electrospinning", Army Research Laboratory, 1999, pp. 1-33, ARL-TR-1989.

Doshi, J. et al., "Electrospinning Process and Applications of Electrospun Fibers", J. Electrostatics, 1995, pp. 151-160, vol. 35.

Ekomedservis: WPI World Patent Information Derwent, Derwent, GB, WPI World Patent Information Derwent, Derwnet, GB, vol. 44, Nr. 95, London, GB, (XP002046663).

Esquivel, C., et al., "Why Small Caliber Vascular Grafts Fail: A Review of Clinical and Experimental Experience and the Significance of the Interaction of Blood at the Interface," J. Surgical Research, 1986, pp. 1-15, vol. 41.

Ferber, D., "Lab-Grown Organs Begin to Take Shape", Science, 1999, pp. 422-424, vol. 284.

Freed, L.E. et al., "Microgravity Tissue Engineering", In Viro Cell. Dev. Biol.—Animal, 1997, pp. 381-385, vol. 33.

Gibson, P.W. et al., "Electrospun Fiber Mats: Transport Properties", U.S. Army Natick Research, Development and Engineering Center, AICHE Journal, 1999, pp. 190, vol. 45.

Gojo, S. et al., "Transplantation of Genetically Marked Cardiac Muscle Cells", J. Thorac. Cardiovasc. Surg., 1997, pp. 10-18, vol. 113.

Gorodetsky, R., "Fibrin Microbeads (FMB) as biodegradable microcarriers for cultured cells and wound healing," ABSTRACT, http://www.Hadassah.org.il/hadasit/patent17.htm, Jun. 14, 2000, pp. 1.

Gospodarowicz, D., et al., "The Extracellular Matrix and the Control of Proliferation of Vascular Endothelial and Vascular Smooth Muscle Cells," J. Supramolecular Structure, 1980, pp. 339-372, vol. 13. (missing pp. 359-372).

Herbert, C.B., et al., "Effects of fibrin micromorphology on neurite growth from dorsal root ganglia cultured in three-dimensional fibrin gels," J. Biomed. Mater. Res., 1998, pp. 551-559, vol. 40.

Hopkins, S.P. et al., "Controlled delivery of vascular endothelial growth factor promotes neovascularization and maintains limb function in a rabbit model of ischemia", J. Vascular Surgery, 1998, pp. 886-895, vol. 27, No. 5.

Huang, L. et al., "Generation of Synthetic Elastin-Mimetic Small Diameter Fibers and Fiber Networks", Macromolecules, 2000, pp. 2989-2997, vol. 33.

Huang, L. et al., "High-Resolution Analysis of Engineered Type I Collagen Nanofibers by Electron Microscopy," Scanning, 2001, pp. 372-375, vol. 23.

Kim, B-S et al., "Optimizing Seeding and Culture Methods to Engineer Smooth Muscle Tissue on Biodegradable Polymer Matrices", Biotechnology Bioengineering, 1998, pp. 46-54, vol. 57.

Kim, B-S et al., "Engineering smooth muscle tissue with a predefined structure", J. Biomed. Mater. Res., 1998, pp. 322-332, vol. 41.

Koh, G.Y. et al., "Long-term survival of AT-1 cardiomyocyte grafts in syngeneic myocardium", Am. Journ. Physiol., 1993, pp. H1727-H1733, vol. 264.

Li, R-K et al., "In Vivo Survival and Function of Transplanted Rat Cardiomyocytes", Circulation Res., 1996, pp. 283-288, vol. 78, No. 2.

Matthews et al., "Vascular Engineering Utilizing Electrospun Collagen," Abstract for Presentation at Engineering Tissues, Hilton Head Island, SC, Feb. 24, 2001.

Matthews et al., "Electroprocessing: Fabrication of Novel Biocompatible Materials," Abstract for Presentation at the 4th International Symposium on Frontiers in Biomedical Polymers, Williamsburg, VA, Presented May 16, 2001.

Mikos, A.G., et al., "Wetting of poly (L-lactic acid) and poly (DL-lactic-co-glycolic acid) foams for tissue culture," Biomaterials, 1994, pp. 55-58, vol. 15, No. 1.

Mooney, D.J., et al., "Design and Fabrication of Biodegradable Polymer Devices To Engineer Tubular Tissues," Cell Transplantation, 1994, pp. 203-210, vol. 3, No. 2.

Morozov, V.N. et al., "Atomic force microscopy of structures produced by electrospraying polymer solutions", International Journal of Mass Spectrometry, 1998, pp. 143-159, vol. 178.

Morozov, V.N. et al., "Electrospray Deposition as a Method to Fabricate Functionally Active Protein Films", Analytical Chem., Apr. 1, 1999, pp. 1415-1420, vol. 71, No. 7.

Murry, C.E. et al., "Skeletal Myoblast Transplantation for Repair of Myocardial Necrosis", J. Clin Invest., 1996, pp. 2512-2523, vol. 98, No. 11.

Niklason, L.E. et al., "Functional Arteries Grown in Vitro", Science, 1999, pp. 489-493, vol. 284.

Okano et al., "Hybrid Muscular Tissues: Preparation of Skeletal Muscle Cell-Incorporated Collagen Gels", Cell Transplantation, 1997, pp. 109-118, vol. 6, No. 2.

Pawlowski et al., "Electrospinning a Biodegradable Vascular Tissue Engineering Scaffold," Abstract for Presentation at the 4th International Symposium on Frontiers in Biomedical Polymers, Williamsburg, VA, Presented May 16, 2001.

Pepper, M.S., "Manipulating Angiogenesis", Arteriosclerosis, Thrombosis, and Vascular Biol., 1997, pp. 605-619, vol. 17.

Pins, G.D. et al., "Self-Assembly of Collagen Fibers Influence of Fibrillar Alignment and Decorin on Mechanical Properties", Biophysical Journal, 1997, pp. 2164-2172, vol. 73.

Pistner, H. et al., "Poly(L-lactide): a long-term degradation study in vivo, Part III Analytical characterization", Biomaterials, 1993, pp. 293-298, vol. 14.

Reneker, D.H. et al., "Nanometer diameter fibres of polymer, produced by electrospinning", Nanotechnology, 1996, pp. 216-223, vol. 7.

Rohr, S. et al., "Patterned Growth of Neonatal Rat Heart Cells in Culture", Circulation Res., 1991, pp. 114-130, vol. 68.

Sabelman, E.E., et al., "Compsite Cell/Tissue Replacement for Nerve and Pressure Sore Repair," http://guide.Stanford.edu/Publications/clinB.html, Jun. 15, 2000, pp. 1-2.

Schreuder-Gibson, H., "Electrospinning Polymer Fibers", www-sscom.army.mil/warrior/97/apr/yarn.html, U.S. Army Natick Research, Development & Engineering Center, 1997.

Shinoka, T. et al., "Creation of Viable Pulmonary Artery Autografts Through Tissue Engineering", J. Thorac. Cardiovasc. Surg., 1998, pp. 536-546, vol. 115.

Simpson, D.G. et al., "Modulation of Cardiac Myocyte Phenotype In Vitro by the Composition and Orientation of the Extracellular Matrix", J. Cellular Physiol., 1994, pp. 89-105, vol. 161.

Soonpaa, M.H. et al., "Formation of Nascent Intercalated Disks Between Grafted Fetal Cardiomyocytes and Host Myocardium", Science, 1994, pp. 98-101, vol. 264.

Stitzel, J.D., et al., "Arterial Smooth Muscle Cell Proliferation on a Novel Biomimicking, Biodegradable Vascular Graft Scaffold," J. Biomaterials Applications, 2001, pp. 1-12, vol. 15.

Stitzel et al., "Electrospraying and Electrospinning of Polymers for Biomedical Applications. Poly (lactic-co-glycolic acid) and Poly (ethylene-co-vinylacetate)." Proc. 32nd Society for the Advancement of Material and Process Engineering (SAMPE) Meeting, Boston, MA, Presented Nov. 7, 2000.

Stitzel, J., Mechanical Design and Development of a Biomimicking, Biodegradable Vascular Graft, Thesis Submitted at Virginia Commonwealth University, Richmond, VA, Aug. 2000, Indexed Feb. 9, 2001.

Telemeco, T. et al., "Electrospinning Applications in Bioengineering: Fabrication of Bio-Engineered Skeletal Muscle," Poster Presentation at Engineering Tissues, Hilton Head Island, SC, Feb. 25, 2001. (Abstracts available Feb. 21, 2001.)

Tiollier, J. et al., "Fibroblast Behavior on Gels of Type, I, III, and IV Human Placental Collagens", Exp. Cell Res., 1990, pp. 95-104, vol. 191.

Vandenburgh, H. et al., "Attenuation of Skeletal Muscle Wasting with Recombinant Human Growth Hormone Secreted from a Tissue-Engineered Bioartificial Muscle", Human Gene Therapy, 1998, pp. 2555-2564, vol. 9.

Van Wachem, P.B. et al., "Myoblast seeding in a collagen matrix evaluated in vitro", J. Biomed. Materials Res., 1996, pp. 353-360, vol. 30.

Warner, S.B.. et al., "A Fundamental Investigation of the Formation and Properties of Electrospun Fibers," National Textile Center Annual Report, Nov. 1999, pp. 1-10.

Watanabe, E. et al., "Cardiomyocyte Transplantation in a Porcine Myocardial Infarction Model", Cell Transplantation, 1998, pp. 239-246, vol. 7, No. 3.

Weinberg, C. et al., "A blood vessel model constructed from collagen and cultured vascular cells," Science, 1986, pp. 397-398, vol. 231.

Weiss, S.W. et al., "Revascularization of Skeletal Muscle Transplanted into the Hamster Cheek Pouch: Electron Microscopy", Microvascular Research, 1983, pp. 65-73, vol. 26.

Wnek, G., Electroactive Materials and Systems: Applications to Fuel Cells and Biosensors. Abstract for Presentation at Molecular Geodesics, Inc., Oct. 13 or 14, 1999.

Wnek, G., "Electroactive Materials and Systems: Applications to Fuel Cells and Biosensors," Abstract for Presentation of Materials Science and Engineering Seminar, Virginia Polytechnic Institute and State University, Blacksburg, VA, Presented Oct. 22, 1999. www.eng.vt.edu/eng/materials/seminars/fall99/wnek.html.

Wnek, G., "Electrospinning of Biomaterials," Abstract of Presentation at University of Massachusetts Lowell Memorial Service and Technical Symposium Honoring Sukant K. Tripathy, Presented in Lowell, MA, Feb. 16, 2001.

Wnek, G.E., Bowlin, G.L., and Simpson, D.G., "Electrospraying and Electrospinning of Polymers for Tissue Engineering/Biomaterials Applications." Abstract for Presentation at Poly Millennial 2000 an International Symposium by the Division of Polymer Chemistry/ American Chemical Society, Hawaii, Presented Dec. 10, 2000.

Wnek, G., "Production of Microfibers by Electrospinning," Abstract for Presentation at Phillip Morris Technical Center, Richmond, VA, Presented Feb. 13, 2001.

Wnek, G., "Thinking Small About Old Polymers at the Medicine/ Engineering Interface," Abstract for Presentation at Program in Polymer Science and Technology Seminar Series, Presented at Massachusetts Institute of Technology, Cambridge, MA, May 16, 2001.

Wnek, G., "Thinking Small About Old Polymers at the Medicine/ Engineering Interface," Abstract for Presentation at Chemical Engineering Seminar, Worcester Polytechnic Institute, Worcester, MA, Presented Oct. 18, 2001.

Wong, W. H. et al., "Synthesis and Properties of Biodegradable Polymers Used as Synthetic Matrices for Tissue Engineering", Synthetic Biodegradable Polymer Scaffolds, 1997, pp. 51-82, Chp. 4.

Yeager, A. et al., "New Graft Materials and Current Approaches to an Acceptable Small Diameter Vascular Graft", ASAIO Transactions, 1988, pp. 88-94, vol. 34.

Zünd, G. et al., "Tissue engineering: A new approach in cardiovascular surgery; Seeding of human fibroblasts followed by human endothelial cells on resorbable mesh," European Journal of Cardiothoracic Surgery, 1998, pp. 160-164, vol. 13.

\* cited by examiner

*Primary Examiner*—Rebecca E. Prouty
*Assistant Examiner*—Rosanne Kosson

(57) ABSTRACT

The invention is directed to novel compositions comprising an electroprocessed material and a substance, their formation and use. The electroprocessed material can, for example, be one or more natural materials, one or more synthetic materials, or a combination thereof. The substance can be one or more therapeutic or cosmetic substances or other compounds, molecules, cells, vesicles. The compositions can be used in substance delivery, including drug delivery within an organism by, for example, releasing substances or containing cells that release substances. The compositions can be used for other purposes, such as prostheses or similar implants.

19 Claims, 8 Drawing Sheets

ELECTROPROCESSED MATERIAL MADE BY SIMULTANEOUSLY ELECTROPROCESSING A NATURAL PROTEIN POLYMER AND TWO SYNTHETIC POLYMERS

PRIOR RELATED APPLICATIONS

This application is a continuation of application Ser. No. 09/982,515, filed Oct. 18, 2001, now abandoned, which is a continuation-in-part of application Ser. No. 09/946,158, filed Sep. 4, 2001, now abandoned, which is a continuation-in-part of application Ser. No. 09/654,517, filed Sep. 1, 2000, now abandoned, application Ser. No. 09/982,515 is a continuation-in-part of application Ser. No. 09/714,255, filed Nov. 17, 2000, now abandoned, which is a continuation-in-part of application Ser. No. 09/512,081, filed Feb. 24, 2000, now abandoned, which is a continuation-in-part of application Ser. No. 09/386,273, filed Aug. 31, 1999, now U.S. Pat. No. 6,592,623, application Ser. No. 09/982,515 filed Oct. 18, 2001 is also a continuation-in-part of application Ser. No. 09/512,081 filed Feb. 24, 2000 now abandoned, application Ser. No. 09/982,515 is also a continuation-in-part of application Ser. No. 09/386,273 filed Aug. 31, 1999, now U.S. Pat. No. 6,592,623, which claims priority to Provisional Application No. 60/241,008, filed Oct. 18, 2000 and Provisional Application No. 60/270,118, filed Feb. 22, 2001.

FIELD OF THE INVENTION

The present invention relates to novel compositions comprising electroprocessed materials with substances, and methods of making and using these compositions in delivery of substances.

BACKGROUND OF THE INVENTION

Numerous methods exist for delivering substances to desired locations in vivo or in vitro. One such method uses devices or objects that contain a substance and will release the substance within a desired location. One desirable application for such methods is the administration of such objects to a location within the body of an organism, followed by the subsequent release of the desired substance into the body. In these examples, the implant often contains the substance and a carrier. After implantation, the substance is released by a variety of means including, for example, diffusion from an implant or dissolution or other degradation of a capsule coat.

Biocompatibility is a desirable attribute in compositions designed for substance delivery. With surgical and subdermal implants, for example, the substance to be delivered is often contained in a matrix comprised of synthetic polymers. Where natural products are used in making bandages, the products typically comprise wood products such as cellulose or other materials that are not readily absorbed by the body of the recipient. Accordingly, such bandages must eventually be removed. Implants compressed from natural materials that may be absorbed by the body are one way to improve biocompatibility and is one area in which improvements are desired.

There is also a continuing need for greater versatility and flexibility in substance delivery technology. Additional techniques for controlling release kinetics and spatial patterns of release or delivery are examples of developments that can improve substance delivery. Implants in which there is refined control of structure at the microscopic or molecular level and overall implant shape are also desired. Such methods could allow, for example, further refinements in control of pore size or other attributes that affect diffusion in and out of a matrix, or more refined control of the distribution of a substance within a matrix. New methods that allow encapsulation of living cells within a matrix are especially desired. Such methods would allow implants to contain, for example, cells that produced desired substances, cells that promote tissue growth, or cells that serve both of these functions.

What is needed therefore are new compositions for use in drug delivery that provide additional and improved methods of controlling configuration of drug delivery systems. Compositions with improved biocompatibility compared to those currently used in substance delivery and/or that can contain living cells are also needed. What is further needed are new methods of substance delivery using such compositions. Finally, methods for making such compositions are also needed.

SUMMARY OF THE INVENTION

The present invention seeks to overcome the limitations in the prior art by providing compositions comprising an electroprocessed material and a substance. The substance may be the material itself, or another substance which may be delivered with the electroprocessed material to a desired site. Sometimes the compositions comprising an electroprocessed material and a substance are in the form of a matrix. The electroprocessed materials include any natural or non-natural materials or blends thereof. The substance is released from the composition or causes the release of molecules or compounds from the composition. Substance release can occur in vitro, in vivo, or both.

The present invention also includes a method for delivery of substances to a location using the present compositions comprising an electroprocessed material and a substance. The locations can be in vitro, in vivo, or both. The invention also includes methods for making the compositions of the present invention.

The compositions of the present invention include an electroprocessed material and a substance. The material can include naturally occurring materials, synthetically manufactured materials, or combinations thereof. Naturally occurring materials include natural organic or inorganic materials, genetically engineered materials and include synthetic alterations thereof. Synthetic materials include materials prepared through any method of artificial synthesis, processing, or manufacture. The invention includes materials that degrade and can absorbed by the body, or will persist in whole or in part and become portions of an extracellular tissue matrix. The compositions may be made using any electroprocessing technique, including but not limited to electrospinning, electroaerosol, electrospraying or electrosputtering techniques, or any combination thereof. Accordingly, electroprocessed droplets, particles, fibers, fibrils, or combinations thereof are all included in the compositions of the present invention. In a preferred embodiment, the electroprocessed materials form a matrix, and in some cases are similar to an extracellular matrix. Matrices may also be formed from materials that can combine to form another material, such as precursor materials. For example, fibrinogen, when combined with thrombin, will form fibrin.

Any material that may be electroprocessed may be used to form an electroprocessed material to be combined, either before, during or after electroprocessing, with a substance, to form the compositions of the present invention. The compositions of the present invention contain one or more substances. The substance includes any type of substance desired, with examples including molecules, cells, objects, or combinations thereof. In some cases, the substance is the electroprocessed material itself. Molecules can be any size, complexity, or type, including both organic or inorganic molecules as well as any combination of molecules. Molecules include naturally occurring and synthetic molecules. Examples of molecules include, but are not limited to therapeutics, cosmetics, nutraceuticals, vitamins, minerals, humectants, molecules produced by cells, including normal cells, abnormal cells, genetically engineered cells and cells modified through any other process. Both eukaryotic and prokaryotic cells are included in the category of substances. Substances also include, without limitation, antigens, antimicrobials, antifungals, molecules that can cause a cellular or physiological response, metals, gases, minerals, ions, and electrically, magnetically and electromagnetically (i.e., light) reactive materials. Cells are derived from natural sources or are cultured in vitro. Combinations of different types or categories of cells can be used. Examples of objects include, but are not limited to, cell fragments, cell debris, organelles and other cellular components, tablets, viruses, vesicles, liposomes, capsules, and other structures that serve as an enclosure for molecules. It is to be understood that the composition of the present invention comprises at least one substance. Accordingly, numerous substances or combinations of similar or different substances may be combined with the electroprocessed material. The substances may be combined with the electroprocessed material through electroprocessing techniques or through other techniques. The invention also includes embodiments in which the composition comprises electroprocessed matrix materials without an additional substance. In that embodiment, the electroprocessed matrix materials may act as a substance.

The invention provides numerous uses for the compositions of the present invention. One preferred use is the delivery of substances. Substance delivery from the compositions of the present invention can occur in vivo, for example upon or within the body of a human or animal. Substance delivery can also occur in vitro, for example within a cell culture apparatus or well. Substances delivered include those substances contained within the compositions, other substances produced by the substance contained in the composition, or both. For example, a substance may be a cell contained within the electroprocessed material, and the cell may synthesize and release one or more molecules. Cells may release molecules in response to signals, so that the molecules are released in a specific desired circumstance. For example, an inducible promoter in an engineered cell within an electroprocessed material may be used to stimulate the expression and or release of a growth factor.

The compositions of the present invention are versatile with respect to control of substance release from the compositions. Release kinetics of substances can be controlled by manipulating a wide variety of matrix parameters. In various embodiments, the release rate, onset of release, release of more than one compound either at the same or different times, creation of gradients of release and spatial patterns of release may be manipulated. Compositions that contain electrical or magnetic materials can be influenced to move, cause motion, or produce a biological activity by applying an electric current or a magnetic field to the composition located on or within a body, or in vitro. Electroprocessed compositions that contain light sensitive components may be designed. These compositions may move or be induced to release or bind substances in response to specific wavelengths of light. Compositions containing nucleic acids or genetically engineered cells, for example, can be used in gene therapy. Other examples include embodiments used in wound care, tissue or organ replacements, and prostheses. In some embodiments, the electroprocessed material itself contains desired properties of substances, and acts as a substance without addition of another substance. The invention thus includes a wide variety of methods of using the compositions of the present invention in medical veterinary, agricultural, research and other applications. The compositions of the present invention provide safer and more predictable release of substances and provide a major advance in the field of substance delivery, especially drug delivery.

The invention also includes methods for making the compositions of the present invention using any type of electroprocessing technique, combination of electroprocessing techniques, or a combination of an electroprocessing technique and another technique, such as aerosol techniques. The method includes streaming, spraying, dropping or projecting one or more solutions, fibers, or suspensions comprising the materials to be electroprocessed toward a target under conditions effective to deposit the materials on a substrate. The substances to be combined with the electroprocessed materials may be electroprocessed toward the target either before, during or after electroprocessing the material. In this manner, the substance may be incorporated within the electroprocessed material during formation, or may coat the electroprocessed material. Accordingly, one or a plurality of sources of materials and substances is used to provide the ingredients for the electroprocessed composition of the present invention. For example, collagen and a polymer such as poly glycolic acid may be electroprocessed through any combination of electrospinning and electrospraying from two sources. At the same time or at selected times thereafter, substances may be provided from other sources: for example, a third source provides a growth factor, a fourth source provides an anti-angiogenic factor, and a fifth source provides genetically altered fibroblasts. These sources of substances may provide the substances through one or more electroprocessing techniques, such as electrospin, electrospray, electroaerosol, electrosputter or any combination thereof. These sources may also provide the substances to the electroprocessed material through non-electroprocessing techniques, such as aerosol delivery, dripping, coating, soaking or other techniques.

In one preferred embodiment, the compositions of the present invention comprise one or more electroprocessed materials that form a matrix combined with at least one substance. Either the source or target is charged, and the other is grounded. The substrate upon which electrodeposition occurs can be the target itself or another object of any shape or type. For example, the substrate can be an object disposed between the orifice and the target. In one embodiment, the substrate is a location on or within an organism, such as a tissue, a wound site, a desired location for substance delivery, or a surgical field in which the composition is to be applied . By manipulating process parameters, compositions of the present invention can be manufactured with a predetermined shape, for example, for depositing the material onto or into a molded substrate. Substrate shape can be manipulated to achieve a specific three-dimensional structure. Targets can also be rotated or otherwise moved or manipulated during electroprocessing to control distribution of the electroprocessed material and, in embodiments involving electroprocessed fibers, the orientation of the fibers. Substances included in the composition can be combined with the matrix material by any means before, during, and/or after electrodeposition.

The electroprocessed compositions may be formed into any desired shape. For purposes of substance delivery, the desired shape is dictated by the application. Non-limiting examples include the following: in the form of a patch for application to the skin; in the form of a wafer or tablet for ingestion; in the form of a wafer for application to a site of removal of a glioma; in the form of a wrap to surround a tumor; in a particulate form for spraying on a surgical site; and in a particulate form for delivery of substances through inhalation.

Accordingly, it is an object of the present invention to overcome the foregoing limitations and drawbacks by providing compositions comprising an electroprocessed material and a substance.

Another object of the present invention is to provide compositions comprising an electroprocessed natural material and a substance.

Yet another object of the present invention is to provide compositions comprising an electroprocessed synthetic material and a substance.

Still another object of the present invention is to provide compositions comprising blends of an electroprocessed natural material, an electroprocessed synthetic material and a substance.

Another object of the present invention is to provide compositions comprising an electroprocessed synthetic material and a substance.

It is an object of the present invention to provide compositions comprising an electroprocessed material and a substance, wherein the substances comprises comprising cells.

Another object of the present invention is to provide compositions comprising an electroprocessed material and a substance, wherein the substance comprises an object.

Still another object of the present invention is to provide compositions comprising an electroprocessed material and a substance, wherein the substance comprises a molecule.

Yet another object of the present invention is to provide compositions comprising an electroprocessed material and a substance, wherein the substance comprises a therapeutic molecule.

Another object of the present invention is to provide compositions comprising an electroprocessed material and substances comprising combinations of cells, molecules, and/or objects.

Another object of the present invention is to provide methods for delivery of a substance to a location, comprising placing the composition of the present invention at a desired location.

Still another object of the present invention is to provide methods for delivery of substances to a location inside or upon the body of a human or animal.

Yet another object of the present invention is to provide methods for retrieval of substances from a location inside or upon the body of a human or animal by bonding such substances.

Yet another object of the present invention is to provide methods for delivery or retrieval of substances to in vitro locations.

Another object of the present invention is to provide methods for delivery of drugs in vivo.

Yet another object of the present invention is to provide methods of administering gene and or peptide therapy.

Another object of the present invention is to provide methods of protein or peptide therapy.

Still another object of the present invention is to provide methods of administering tissue and organ replacements and prostheses.

Another object of the present invention is to provide methods for making the compositions of the present inventions.

These and other objects, features and advantages of the present invention will become apparent after a review of the following detailed description of the disclosed embodiments and the appended drawings.

DETAILED DESCRIPTION OF THE PREFERRED EMBODIMENTS

Figure 1:
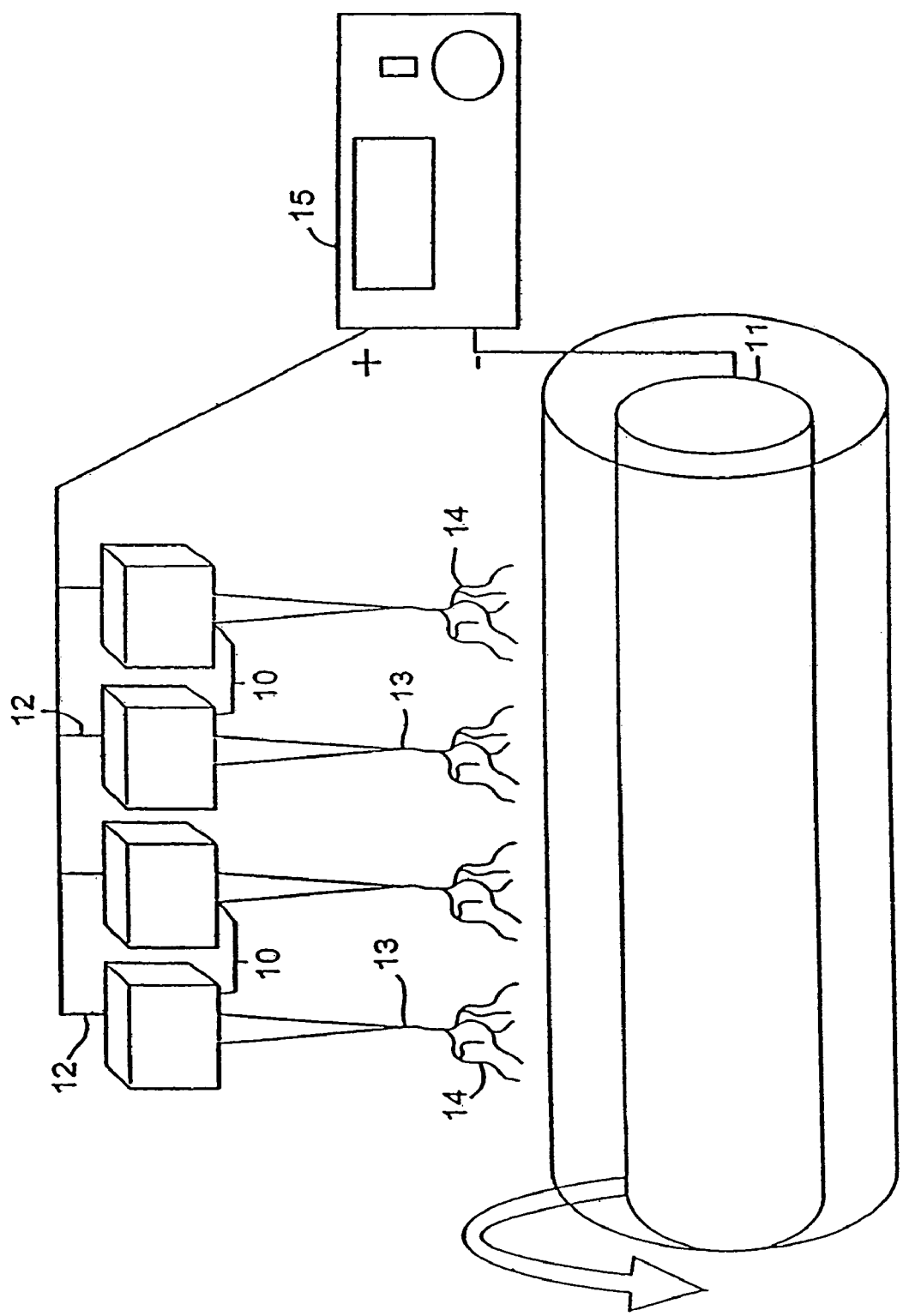
FIG. 1 is a schematic drawing of an embodiment of an electroprocessing device including the electroprocessing equipment and a rotating wall bioreactor.

The term "substance" shall be used throughout this application in its broadest definition. The term substance includes one or more molecules, objects, or cells of any type or size, or combinations thereof. Substances can be in any form including, but not limited to solid, semisolid, wet or dry mixture, gas, solution, suspension, combinations thereof. Substances include molecules of any size and in any combination. Cells include all cell types of prokaryotic and eukaryotic cells, whether in natural state or altered by genetic engineering or any other process. Cells can be from a natural source or cultured in vitro and can be living or dead. Combinations of different types of cells can be used. Objects can be of any size, shape, and composition that may be combined with or coupled to an electroprocessed material. Examples of objects include, but are not limited to, cell fragments, cell debris, fragments of cell walls, fragments of viral walls, organelles and other cell components, tablets, viruses, vesicles, liposomes, capsules, nanoparticulates, and other structures that serve as an enclosure for molecules. The compositions of the present invention may comprise one substance or any combination of substances.

The terms "electroprocessing" and "electrodeposition" shall be defined broadly to include all methods of electrospinning, electrospraying, electroaerosoling, and electrosputtering of materials, combinations of two or more such methods, and any other method wherein materials are streamed, sprayed, sputtered or dripped across an electric field and toward a target. The electroprocessed material can be electroprocessed from one or more grounded reservoirs in the direction of a charged substrate or from charged reservoirs toward a grounded target. "Electrospinning" means a process in which fibers are formed from a solution or melt by streaming an electrically charged solution or melt through an orifice. "Electroaerosoling" means a process in which droplets are formed from a solution or melt by streaming an electrically charged polymer solution or melt through an orifice. The term electroprocessing is not limited to the specific examples set forth herein, and it includes any means of using an electrical field for depositing a material on a target.

The term "material" refers to any compound, molecule, substance, or group or combination thereof that forms any type of structure or group of structures during or after electroprocessing. Materials include natural materials, synthetic materials, or combinations thereof. Naturally occurring organic materials include any substances naturally found in the body of plants or other organisms, regardless of whether those materials have or can be produced or altered synthetically. Synthetic materials include any materials prepared through any method of artificial synthesis, processing, or manufacture. Preferably the materials are biologically compatible materials.

One class of synthetic materials, preferably biologically compatible synthetic materials, comprises polymers. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, and polyorthoesters or any other similar synthetic polymers that may be developed that are biologically compatible. The term "biologically compatible, synthetic polymers" shall also include copolymers and blends, and any other combinations of the forgoing either together or with other polymers generally. The use of these polymers will depend on given applications and specifications required. A more detailed discussion of these polymers and types of polymers is set forth in Brannon-Peppas, Lisa, "Polymers in Controlled Drug Delivery," *Medical Plastics and Biomaterials*, November 1997, which is incorporated by reference as if set forth fully herein.

"Materials" also include electroprocessed materials that are capable of changing into different materials during or after electroprocessing. For example, the protein fibrinogen, when combined with thrombin, forms fibrin. Fibrinogen or thrombin that are electroprocessed as well as the fibrin that later forms are included within the definition of materials. Similarly, procollagen will form collagen when combined with procollagen peptidase. Procollagen, procollagen peptidase, and collagen are all within the definition.

In a preferred embodiment, the electroprocessed materials form a matrix. The term "matrix" refers to any structure comprised of electroprocessed materials. Matrices are comprised of fibers, or droplets of materials, or blends of fibers and droplets of any size or shape. Matrices are single structures or groups of structures and can be formed through one or more electroprocessing methods using one or more materials. Matrices are engineered to possess specific porosities. Substances may be deposited within, or anchored to or placed on matrices. Cells are substances which may be deposited within or on matrices.

One preferred class of materials for electroprocessing to make the compositions of the present invention comprises proteins. Extracellular matrix proteins are a preferred class of proteins in the present invention. Examples include but are not limited to collagen, fibrin, elastin, laminin, and fibronectin. Additional preferred materials are other components of the extracellular matrix, for example proteoglycans. In each case, those names are used throughout the present application in their broadest definition. There are multiple types of each of these proteins that are naturally-occurring as well as types that can be or are synthetically manufactured or produced by genetic engineering. For example, collagen occurs in many forms and types. All of these types and subsets are encompassed in the use of the proteins named herein. The term protein further includes, but is not limited to, fragments, analogs, conservative amino acid substitutions, and substitutions with non-naturally occurring amino acids with respect to each named protein. The term "residue" is used herein to refer to an amino acid (D or L) or an amino acid mimetic that is incorporated into a protein by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

It is to be understood that the term protein, polypeptide or peptide further includes fragments that may be 90 to 95% of the entire amino acid sequence, and also extensions to the entire amino acid sequence that are 5% to 10% longer than the amino acid sequence of the protein, polypeptide or peptide.

When peptides are relatively short in length (i.e, less than about 50 amino acids), they are often synthesized using standard chemical peptide synthesis techniques. Solid phase synthesis in which the C terminal amino acid of the sequence is attached to an insoluble support followed by sequential addition of the remaining amino acids in the sequence is a preferred method for the chemical synthesis of the antigenic epitopes described herein. Techniques for solid phase synthesis are known to those skilled in the art.

Alternatively, the proteins or peptides that may be electroprocessed are synthesized using recombinant nucleic acid methodology. Generally, this involves creating a nucleic acid sequence that encodes the peptide or protein, placing the nucleic acid in an expression cassette under the control of a particular promoter, expressing the peptide or protein in a host, isolating the expressed peptide or protein and, if required, renaturing the peptide or protein. Techniques sufficient to guide one of skill through such procedures are found in the literature.

When several desired protein fragments or peptides are encoded in the nucleotide sequence incorporated into a vector, one of skill in the art will appreciate that the protein fragments or peptides may be separated by a spacer molecule such as, for example, a peptide, consisting of one or more amino acids. Generally, the spacer will have no specific biological activity other than to join the desired protein fragments or peptides together, or to preserve some minimum distance or other spatial relationship between them. However, the constituent amino acids of the spacer may be selected to influence some property of the molecule such as the folding, net charge, or hydrophobicity. Nucleotide sequences encoding for the production of residues which may be useful in purification of the expressed recombinant protein may be built into the vector. Such sequences are known in the art. For example, a nucleotide sequence encoding for a poly histidine sequence may be added to a vector to facilitate purification of the expressed recombinant protein on a nickel column.

Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents.

Also, molecules capable of forming some of the named proteins can be mixed with other polymers during electroprocessing to obtain desired properties for uses of the formed protein in the matrix.

Throughout this application the term "solution" is used to describe the liquid in the reservoirs of the electroprocessing method. The term is defined broadly to include any liquids that contain materials to be electroprocessed. It is to be understood that any solutions capable of forming a material during electroprocessing are included within the scope of the present invention. In this application, the term "solution" also refers to suspensions or emulsions containing the material or anything to be electrodeposited. "Solutions" can be in organic or biologically compatible forms. This broad definition is appropriate in view of the large number of solvents or other liquids and carrier molecules, such as polyethylene glycol (PEG), that can be used in the many variations of electroprocessing. In this application, the term "solution" also refers to melts, hydrated gels and suspensions containing the materials, substances or anything to be electrodeposited.

Solvents

Any solvent that will allows delivery of the material or substance to the orifice or tip of a syringe under such conditions that the material or substance will be processed as desired may be used for dissolving or suspending the material or the substance to be electroprocessed. Solvents useful for dissolving or suspending a material or a substance will depend on the material or substance. Electrospinning techniques often require more specific solvent conditions. For example, non cross-linked fibrin monomer can be electrodeposited or electrospun from solvents such as urea, monochloroacetic acid, water, 2,2,2-trifluoroethanol, or 1,1,1,3,3,3-hexafluoro-2-propanol (also known as hexafluoroisopropanol or HFIP). Collagen can be electrodeposited as a solution or suspension in water, 2,2,2-trifluoroethanol, or HFIP. Elastin can be electrodeposited as a solution or suspension in water, 2,2,2-trifluoroethanol, isopropanol, or HFIP. Other lower order alcohols, especially halogenated alcohols, may be used. Proteins and peptides associated with membranes are often hydrophobic and thus cannot dissolve in aqueous solutions. Such proteins can be dissolved in organic solvents such as methanol, chloroform, and trifluoroethanol (TFE). Any other solvents known to one of skill in the protein chemical art may be used, for example solvents useful in chromatography, especially high performance liquid chromatography. Proteins and peptides are also soluble, for example, in HFIP, hexafluoroacetone, chloroalcohols in conjugation with aqueous solutions of mineral acids, dimethylacetamide containing 5% lithium chloride, in very dilute acids such as acetic acid and formic acid. N-methyl morpholine-N-oxide is another solvent that can be used with many polypeptides.

In functional terms, solvents used for electroprocessing have the principal role of creating a mixture with a polymer, or polymers, such that electroprocessing is feasible. The concentration of a given solvent is often an important consideration in determining the type of electroprocessing that will occur. For example, in electrospraying, the solvent should assist in the dispersion of droplets of electroprocessed material so that the initial jet of liquid disintegrates into droplets. Accordingly, solvents used in electrospraying should not create forces that will stabilize an unconfined liquid column. In electrospinning, interactions between molecules of electroprocessed material stabilize the jet, leading to fiber formation. Accordingly, for electrospun embodiments, the solvent should sufficiently dissolve or disperse the polymer to prevent the jet from disintegrating into droplets and should thereby allow formation of a stable jet in the form of a fiber. In some embodiments, the transition from electrospraying to electrospinning can be determined by examining Brookfield viscosity measurements for polymer solutions as a function of concentration. Brookfield viscosity increases as concentration of a polymer or other material to be electroprocessed increases. Above a critical concentration associated with extensive chain entanglements of materials, however, the Brookfield viscosity will increase more rapidly with concentration, as opposed to a more gradual, linear rise with concentration at lower concentrations. For example, the Brookfield viscosity of a poly(lactide) sample obtained from Alkermes dissolved in chloroform shows an upturn in the Brookfield viscosity/concentration plot at approximately 7-8% w/v. A sample of poly(ethylene-co-vinyl acetate) from Dupont (ELVAX 40W) shows an upturn at 14-15% w/v . In both cases, these departures from linearity approximately coincide with the transition from electrospraying to electrospinning.

Compositions of the Present Invention

The Electroprocessed Material

One component of the compositions of the present invention is the electroprocessed material. As defined above, the electroprocessed material of the present invention can include natural materials, synthetic materials, or combinations thereof. Examples include but are not limited to amino acids, peptides, denatured peptides such as gelatin from denatured collagen, polypeptides, proteins, carbohydrates, lipids, nucleic acids, glycoproteins, lipoproteins, glycolipids, glycosaminoglycans, and proteoglycans.

Some preferred materials are naturally occurring extracellular matrix materials and blends of naturally occurring extracellular matrix materials, including but not limited to collagen, fibrin, elastin, laminin, fibronectin, hyaluronic acid, chondroitin 4-sulfate, chondroitin 6-sulfate, dermatan sulfate, heparin sulfate, heparin, and keratan sulfate, and proteoglycans. These materials may be isolated from humans or other animals or cells or synthetically manufactured. Some especially preferred natural matrix materials are collagen and fibrin and fibronectin. Also included are crude extracts of tissue, extracellular matrix material, extracts of nonnatural tissue, or extracellular matrix materials (i.e. extracts of cancerous tissue), alone or in combination. Extracts of biological materials, including but not limited to cells, tissues, organs, and tumors may also be electroprocessed. Collagen has been electrospun to produce a repeating, banded pattern observed with electron microscopy. This banded pattern is typical of collagen fibrils produced by natural processes (i.e. banded pattern is observed in collagen when it is produced by cells). In some embodiments, collagen is electrospun such that it has a 65 nm banding pattern.

It is to be understood that these electroprocessed materials may be combined with other materials and/or substances in forming the compositions of the present invention. For example, an electroprocessed peptide may be combined with an adjuvant to enhance immunogenicity when implanted subcutaneously. As another example, an electroprocessed collagen matrix, containing cells, may be combined with an electroprocessed biologically compatible polymer and growth factors to stimulate growth and division of the cells in the collagen matrix.

Synthetic materials include any materials prepared through any method of artificial synthesis, processing, or manufacture. The synthetic materials are preferably biologically compatible for administration in vivo or in vivo. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO) and polyorthoesters or any other similar synthetic polymers that may be developed that are biologically compatible. Some preferred synthetic matrix materials include PLA, PGA, copolymers of PLA and PGA, polycaprolactone, poly(ethylene-co-vinyl acetate), (EVOH), PVA, and PEO. Matrices can be formed of electrospun fibers, electroaerosol, electrosprayed, or electrosputtered droplets, or a combination of the foregoing.

In embodiments in which natural materials are used, those materials can be derived from a natural source, synthetically manufactured, or manufactured by genetically engineered cells. For example, genetically engineered proteins can be prepared with specific desired sequences of amino acids that differ from the natural proteins. In one illustrative embodiment, desirable sequences that form binding sites on a collagen protein for cells or peptides can be included in higher amounts than found in natural collagen.

By selecting different materials, or combinations thereof, many characteristics of the electroprocessed material can be manipulated. The properties of the matrix comprised of electroprocessed material and a substance may be adjusted. As discussed in greater detail below, electroprocessed materials themselves can provide a therapeutic effect when applied. In addition, selection of matrix materials can affect the permanency of an implanted matrix. For example, matrices made of fibrin will degrade more rapidly while matrices made of collagen are more durable and synthetic matrix materials are more durable still. Use of matrices made of natural materials such as proteins also minimize rejection or immunological response to an implanted matrix. Accordingly selection of materials for electroprocessing and use in substance delivery is influenced by the desired use. In one embodiment, a skin patch of electroprocessed fibrin or collagen combined with healing promoters and anti-rejection substances may be applied to the skin and may subsequently dissolve into the skin. In another embodiment, an implant for delivery to bone may be constructed of materials useful for promoting bone growth, osteoblasts and hydroxyapatite, and may be designed to endure for a prolonged period of time.

Synthetic components, such as biocompatible substances can be used to modulate the release of materials from an electroprocessed composition. For example, a drug, or series of drugs or other materials to be released in a controlled fashion can be electroprocessed into a series of layers. One layer is composed of PGA plus a drug, the next layer PLA plus a drug, a third layer is composed of polycaprolactone plus a drug. The layered construct can be implanted, and as the successive layers dissolve or breakdown, the drug (or drugs) is released in turn as each successive layer erodes. Unlayered structures can also be used, and release is controlled by the relative stability of each component of the construct. Another advantage of the synthetic materials is that different solvents can be used. This can be important for the delivery of some materials. For example, a drug may be soluble in some organics, and using synthetics increases the number of materials that can be electroprocessed. The breakdown of these synthetic materials can be tailored and regulated in ways that are not available to natural materials. The synthetics are usually not subject to enzymatic breakdown, and many spontaneously undergo hydrolysis. In addition to these characteristics, substances can be released from electroprocessed materials in response to electrical, magnetic and light based signals. Polymers that are sensitive to such signals can be used, or the polymers may be derivatized in a way to provide such sensitivity. These properties provide flexibility in making and using electroprocessed materials designed to deliver various substances, in vivo and in vitro.

In some embodiments of the present invention, the electroprocessed material itself provides a therapeutic effect. For example, in some embodiments electroprocessed collagen promotes cellular infiltration and differentiation, so an electroprocessed collagen matrix alone assists with healing. The P-15 site, a 15 amino acid sequence within the collagen molecule, promotes osteoblasts to produce and to secrete hydroxyapatite, a component of bone. Another example of specific sites and sequences within collagen molecules that can be manipulated and processed in a similar fashion includes the RGD binding sites of the integrin molecule. The RGD site is a sequence of three amino acids (Arg-Gly-Asp) present in many matrix materials that serves as a binding site for cell adhesion. It is recognized and bound, for example, by integrins. In addition, electroprocessed materials can be enriched with specific desired sequences before, during, or after electroprocessing. Sequences can be added in linear or other forms. In some embodiments, the RGD sequences are arranged in a cyclic form referred to as cycloRGD.

An electroprocessed material, such as a matrix, can also be composed of specific subdomains of a matrix constituent and can be prepared with a synthetic backbone that can be derivatized. For example, the RGD peptide sequence, and/or a heparin binding domain and/or other sequences, can be chemically coupled to synthetic materials. The synthetic polymer with the attached sequence or sequences can be electroprocessed into a construct. This produces a matrix with unique properties. In these examples the RGD site provides a site for cells to bind to and interact with the matrix. The heparin-binding site provides a site for the anchorage of peptide growth factors to the synthetic backbone. Angiogenic peptides, genetic material, growth factors, cytokines, enzymes and drugs are other non-limiting examples of substances that can be attached to the backbone of an electroprocessed material to provide functionality. Peptide side chains may also be used to attach molecules to functional groups on polymeric backbones. Molecules and other substances can be attached to a material to be electroprocessed by any technique known in the art.

Another embodiment of matrix materials that have a therapeutic effect is electroprocessed fibrin. Fibrin matrix material assists in arrest of bleeding. Fibrin is a component of the provisional matrix that is laid down during the early stages of healing and may also promote the growth of vasculature in adjacent regions, and in many other ways is a natural healing promoter. Fibrinogen as an electroprocessed material can also assist in healing. When placed in contact with a wound, for example, fibrinogen will react with thrombin present in the blood plasma from the wound and form fibrin, thereby providing the same healing properties of a fibrin material.

Substances

As discussed above, the word "substance" in the present invention is used in its broadest definition. In embodiments in which the compositions of the present invention comprise one or more substances, substances can include any type or size of molecules, cells, objects or combinations thereof. The compositions of the present invention may comprise one substance or any combination of substances.

In embodiments in which the substances are molecules, any molecule can be used. Molecules may, for example, be organic or inorganic and may be in a solid, semisolid, liquid, or gas phase. Molecules may be present in combinations or mixtures with other molecules, and may be in solution, suspension, or any other form. Examples of classes of molecules that may be used include human or veterinary therapeutics, cosmetics, nutraceuticals, agriculturals such as herbicides, pesticides and fertilizers, vitamins, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, minerals, ions, electrically and magnetically reactive materials, light sensitive materials, antioxidants, molecules that may be metabolized as a source of cellular energy, antigens, and any molecules that can cause a cellular or physiological response. Any combination of molecules can be used as well as agonists or antagonists.

Several preferred embodiments use therapeutic molecules include use of any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmondics, appetite suppressants, neuroactive substances, neurotransmitter agonists, antagonists, receptor blockers and reuptake modulators, beta-adrenergic blockers, calcium channel blockers, disulfarim and disulfarim-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antithrombogenic agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

Antibiotics useful in the present invention include, but are not limited to, amoxicillin, amphotericin, ampicillin, bacitracin, beclomethasone, benzocaine, betamethasone, biaxin, cephalosporins, chloramphenicol, ciprofloxacin, clotrimazole, cyclosporin, docycline, enoxacin, erythromycin, gentamycin, miconazole, neomycin, norfloxacin, nystatin, ofloxacin, pefloxacin, penicillin, pentoxifylline, phenoxymethylpenicillin, polymixin, rifampicin, tetracycline, tobrmycin, triclosan, vancomycin, zithromax, derivatives, metabolites, and mixtures thereof, or compounds having similar antimicrobial activity.

Some specific examples of pharmaceutical agents that are useful as substances include, but are not limited to, quinolones, such as oxolinic acid, norfloxacin, and nalidixic acid, sulfonamides, nonoxynol 9, fusidic acid, cephalosporins, cyclosporine, acebutolol, acetylcysteine, acetylsalicylic acid, acyclovir, AZT, alprazolam, alfacalcidol, allantoin, allopurinol, ambroxol, amikacin, amiloride, aminoacetic acid, aminodarone, amitriptyline, amlodipine, ascorbic acid, aspartame, astemizole, atenolol, benserazide, benzalkonium hydrochloride, benzoic acid, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefatroxil, cefazolin, cefixime, cefotaxime, ceftazidime, ceftriaxone, cefuroxime, selegiline, chloramphenicol, chlorpheniramine, chlortalidone, choline, cilastatin, cimetidine, cisapride, cisplatin, clarithromycin, clavulanic acid, clomipramine, clozapine, clonazepam, clonidine, codeine, cholestyramine, cromoglycic acid, cyanocobalamin, cyproterone, desogestrel, dexamethasone, dexpanthenol, dextromethorphan, dextropropoxiphen, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, Gingko biloba, glibenclamide, glipizide, Glycyrrhiza glabra, grapefruit seed extract, grape seed extract, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, Nmethylephedrine, naffidrofuryl, naproxen, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, omeprazole, ondansetron, pancreatin, panthenol, pantothenic acid, paracetamol, phenobarbital, derivatives, metabolites, and other such compounds have similar activity. Some preferred drugs or compounds include, but are not limited to, estrogen, androgen, cortisone, and cyclosporin.

Growth factors useful in the present invention include, but are not limited to, transforming growth factor-α ("TGF-α"), transforming growth factors ("TGF-β"), platelet-derived growth factors ("PDGF"), fibroblast growth factors ("FGF"), including FGF acidic isoforms 1 and 2, FGF basic form 2 and FGF 4, 8, 9 and 10, nerve growth factors ("NGF") including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, beta3, skeletal growth factor, bone matrix derived growth factors, and bone derived growth factors and mixtures thereof.

Cytokines useful in the present invention include, but are not limited to, cardiotrophin, stromal cell derived factor, macrophage derived chemokine (MDC), melanoma growth stimulatory activity (MGSA), macrophage inflammatory proteins 1 alpha (MIP-1alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, TNF-α, and TNF-β. Immunoglobulins useful in the present invention include, but are not limited to, IgG, IgA, IgM, IgD, IgE, and mixtures thereof. Some preferred growth factors include VEGF (vascular endothelial growth factor), NGFs (nerve growth factors), PDGF-AA, PDGF-BB, PDGF-AB, FGFb, FGFa, and BGF.

Other molecules useful as substances in the present invention include but are not limited to growth hormones, leptin, leukemia inhibitory factor (LIF), tumor necrosis factor alpha and beta, endostatin, thrombospondin, osteogenic protein-1, bone morphogenetic proteins 2 and 7, osteonectin, somatomedin-like peptide, osteocalcin, , interferon alpha, interferon alpha A, interferon beta, interferon gamma, interferon 1 alpha, and interleukins 2, 3, 4, 5 6, 7, 8, 9, 10, 11, 12,13, 15, 16, 17 and 18.

Embodiments involving amino acids, peptides, polypeptides, and proteins may include any type or combinations of such molecules of any size and complexity. Examples include, but are not limited to structural proteins, enzymes, and peptide hormones. These compounds can serve a variety of functions. In some embodiments, the matrix may contain peptides containing a sequence that suppresses enzyme activity through competition for the active site. In other applications antigenic agents that promote an immune response and invoke immunity can be incorporated into a construct.

In substances such as nucleic acids, any nucleic acid can be present. Examples include, but are not limited to deoxyribonucleic acid (DNA), ent-DNA, and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787,567). DNA can be present in vectors of any kind, for example in a viral or plasmid vector. In some embodiments, nucleic acids used will serve to promote or to inhibit the expression of genes in cells inside and/or outside the electroprocessed matrix. The nucleic acids can be in any form that is effective to enhance its uptake into cells.

Cells as a Substance

In embodiments in which cells are a substance, any cell can be used. Cells that can be used include, but are not limited to stem cells, committed stem cells, and differentiated cells. Examples of stem cells that can be used include but are not limited to embryonic stem cells, bone marrow stem cells and umbilical cord stem cells. Other examples of cells used in various embodiments include but are not limited to: osteoblasts, myoblasts, neuroblasts, fibroblasts, glioblasts; germ cells, hepatocytes, chondrocytes, keratinocytes, smooth muscle cells, cardiac muscle cells, connective tissue cells, epithelial cells, endothelial cells, hormone-secreting cells, cells of the immune system, and neurons. In some embodiments it is unnecessary to pre-select the type of stem cell that is to be used, because many types of stem cells can be induced to differentiate in an organ specific pattern once delivered to a given organ. For example, a stem cell delivered to the liver can be induced to become a liver cell simply by placing the stem cell within the biochemical environment of the liver. Cells in the matrix can serve the purpose of providing scaffolding or seeding, producing certain compounds, or both.

Embodiments in which the substance comprises cells include cells that can be cultured in vitro, derived from a natural source, or produced by any other means. Any natural source of prokaryotic or eukaryotic cells may be used. Embodiments in which the matrix is implanted in an organism can use cells from the recipient, cells from a conspecific donor or a donor from a different species, or bacteria or microbial cells. Cells harvested from a source and cultured prior to use are also included.

Some embodiments use cells that have been genetically engineered. The engineering involves programming the cell to express one or more genes, repressing the expression of one or more genes, or both. One example of genetically engineered cells useful in the present invention is a genetically engineered cell that makes and secretes one or more desired molecules. When electroprocessed matrices comprising genetically engineered cells are implanted in an organism, the molecules produced can produce a local effect or a systemic effect, and can include the molecules identified above as possible substances. Cells can also produce antigenic materials in embodiments in which one of the purposes of the matrix is to produce an immune response. Cells may produce substances to aid in the following non-inclusive list of purposes: inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace the following tissue, neurons, skin, synovial fluid, tendons, cartilage, ligaments, bone, muscle, organs, dura, blood vessels, bone marrow, and extracellular matrix.

Genetic engineering can involve, for example, adding or removing genetic material to or from a cell, altering existing genetic material, or both. Embodiments in which cells are transfected or otherwise engineered to express a gene can use transiently or permanently transfected genes, or both. Gene sequences may be full or partial length, cloned or naturally occurring.

Substances in the electroprocessed compositions of the present invention also comprise objects. Examples of objects include, but are not limited to, cell fragments, cell debris, organelles and other cell components, tablets, and viruses as well as vesicles, liposomes, capsules, nanoparticles, and other structures that serve as an enclosure for molecules. In some embodiments, the objects constitute vesicles, liposomes, capsules, or other enclosures that contain compounds that are released at a time after electroprocessing, such as at the time of implantation or upon later stimulation or interaction. In one illustrative embodiment, transfection agents such as liposomes contain desired nucleotide sequences to be incorporated into cells that are located in or on the electroprocessed material or matrix. In other embodiments, cell fragments or cell debris are incorporated into the matrix. The presence of cell fragments is known to promote healing in some tissues.

Magnetically or electrically reactive materials are also examples of substances that are optionally included within compositions of the present invention. Examples of magnetically active materials include but are not limited to carbon black or graphite, carbon nanotubes, ferrofluids (colloidal suspensions of magnetic particles), and various dispersions of electrically conducting polymers. Ferrofluids containing particles approximately 10 nm in diameter, polymer-encapsulated magnetic particles about 1-2 microns in diameter, and polymers with a glass transition temperature below room temperature are particularly useful. Examples of electrically active polymers include, but are not limited to, electrically conducting polymers such as polyanilines, polypyrroles and ionically conducting polymers such as sulfonated polyacrylamides are related materials.

In other embodiments, some substances in the electroprocessed material or matrix supplement or augment the function of other substances. For example, when the composition comprises cells that express a specific gene, the composition can contain oligonucleotides that are taken up by the cells and affect gene expression in the cells. Fibronectin is optionally incorporated into the matrix to increase cellular uptake of oligonucleotides by pinocytosis.

As discussed in detail above, the electroprocessed material itself can provide a therapeutic effect. The invention thus includes embodiments involving methods of causing a therapeutic effect through delivery of an electroprocessed material to a location without incorporating additional substances in the electroprocessed material. Embodiments in which the matrix material alone is delivered as well as those in which other substances are included in the matrix are within the scope of the present invention.

Methods of Making the Composition

Electroprocessing

The method of making the compositions includes electroprocessing the materials and optionally electroprocessing the substances. As defined above, one or more electroprocessing techniques, such as electrospin, electrospray, electroaerosol, electrosputter or any combination thereof may be employed to make the electroprocessed materials and matrices in the compositions of the present invention. In the most fundamental sense, the electroprocessing apparatus for electroprocessing material includes a electrodepositing mechanism and a target substrate. The electrodepositing mechanism includes a reservoir or reservoirs to hold the one or more solutions that are to be electroprocessed or electrodeposited. The reservoir or reservoirs have at least one orifice or nozzle to allow the streaming of the solution from the reservoirs. One or a plurality of nozzles may be configured in an electroprocessing apparatus. If there are multiple nozzles, each nozzle is attached to one or more reservoirs containing the same or different solutions. Similarly, there can be a single nozzle that is connected to multiple reservoirs containing the same or different solutions. Multiple nozzles may be connected to a single reservoir. Because different embodiments involve single or multiple nozzles and/or reservoirs, any references herein to one or nozzles or reservoirs should be considered as referring to embodiments involving single nozzles, reservoirs, and related equipment as well as embodiments involving plural nozzles, reservoirs, and related equipment. The size of the nozzles can be varied to provide for increased or decreased flow of solutions out of the nozzles. One or more pumps used in connection with the reservoirs can be used to control the flow of solution streaming from the reservoir through the nozzle or nozzles. The pump can be programmed to increase or decrease the flow at different points during electroprocessing. In this invention pumps are not necessary but provide a useful method to control the rate at which material is delivered to the electric field for processing. Material can be actively delivered to the electric field as a preformed aerosol using devices such as air brushes, thereby increasing the rate of electrodeposition and providing novel combinations of materials. Nozzles may be programmed to deliver material simultaneously or in sequence.

The electroprocessing occurs due to the presence of a charge in either the orifices or the target, while the other is grounded. In some embodiments, the nozzle or orifice is charged and the target is shown to be grounded. Those of skill in the electroprocessing arts will recognize that the nozzle and solution can be grounded and the target can be electrically charged. The creation of the electrical field and the effect of the electrical field on the electroprocessed materials or substances that will form the electroprocessed composition.

The target substrate can also be used as a variable feature in the electroprocessing of materials used to make the electroprocessed composition. Specifically, the target can be the actual substrate for the materials used to make electroprocessed matrix, or electroprocessed matrix itself is deposited. Alternatively, a substrate can be disposed between the target and the nozzles. For instance, a petri dish can be disposed between a nozzles and a target, and a matrix can be formed in the dish. Other variations include but are not limited to non-stick surfaces between the nozzles and target and placing tissues or surgical fields between the target and nozzles. The target can also be specifically charged or grounded along a preselected pattern so that the solution streamed from the orifice is directed into specific directions. The electric field can be controlled by a microprocessor to create an electroprocessed matrix having a desired geometry. The target and the nozzle or nozzles can be engineered to be movable with respect to each other thereby allowing additional control over the geometry of the electroprocessed matrix to be formed. The entire process can be controlled by a microprocessor that is programmed with specific parameters that will obtain a specific preselected electroprocessed matrix. It is to be understood that any electroprocessing technique may be used, alone or in combination with another electroprocessing technique, to make the compositions of the present invention.

Any material that can be electroprocessed is within the method of the present invention. Forms of electroprocessed collagen include but are not limited to preprocessed collagen in a liquid suspension or solution, gelatin, particulate suspension, or hydrated gel. An example for fibrin is a preformed gel electroprocessed by subjecting it to pressure, for example by using a syringe or airbrush apparatus with a pressure head behind it to extrude the fibrin gel into the electrical field. In general, when producing fibers using electroprocessing techniques, especially electrospinning, it is preferable to use the monomer of the polymer fiber to be formed. In some embodiments it is desirable to use monomers to produce finer filaments. In other embodiments, it is desirable to include partial fibers to add material strength to the matrix and to provide additional sites for incorporating substances. Matrix materials such as collagen in a gelatin form may be used to improve the ability of the material to dissolve. Acid extraction method can be used in preparing such gels to maintain the structure of the monomeric subunits. Units can then be treated with enzymes to alter the structure of the monomers.

In embodiments in which two materials combine to form a third material, the solutions containing these components can be mixed together immediately before they are streamed from an orifice in the electroprocessing procedure. In this way, the third material forms literally as the microfibers or microdroplets are formed in the electrospinning process. Alternatively, such matrices can be formed by electrospraying a molecule that can form matrix materials into a moist or otherwise controlled atmosphere of other molecules necessary to allow formation of the matrix to form filaments within the electric field. For example, fibrinogen can be sprayed into a moist atmosphere of thrombin. Materials such as fibrinogen that are capable of forming other materials such as fibrin can also be electrosprayed onto a target that has thrombin. Alternatively thrombin can also be electrosprayed onto a target that has fibrinogen.

In embodiments in which two or more matrix materials are combined to form a third (for example, combining fibrinogen and thrombin to form fibrin) the matrix materials can be electroprocessed in conjunction with or separately from each other, typically under conditions that do not allow the two molecules to form the third until the desired time. This can be accomplished several ways. Using fibrinogen and thrombin as an example, the two matrix materials can be electroprocessed from a solvent that does not allow thrombin to function. Alternatively, the fibrinogen or thrombin can be packaged in a carrier material. In this application the fibrinogen is electroprocessed onto the target from one solution source (by itself or with a carrier), and the thrombin is deposited in an electroaerosol manner from a separate source. The thrombin can be encapsulated and sprayed as a fine mist of particles. Alternatively, thrombin and fibrinogen can be mixed with a carrier, such as PEG, or other synthetic or natural polymers such as collagen. The carrier acts to hold the reactants in place until they are initiated. These methods are not limited to thrombin and fibrinogen and also are used with embodiments involving other combinations of matrix materials that combine to form a third material. The entire product is preferably stored under dry conditions to prevent the reaction of the two materials. When the material is placed in a moist environment, the materials are able to combine and the product matrix material is formed.

As stated above, it is to be understood that carriers can be used in conjunction with matrix materials. Different materials, such as extracellular matrix proteins, and or substances, can be mixed with PEG or other known carriers that form filaments. For example, fibrinogen and collagen can be mixed with PEG or other known carriers that form filaments. This produces "hairy filaments" with the hair being fibrin. The "hairs" cross-link the surrounding matrix carrier into a gel, or provide reactive sites for cells to interact with the substance within the matrix carrier, such as immunoglobulins. This approach can be used for forming a matrix or gelling molecules that do not normally gel. For example, in embodiments in which a specific type of matrix material will not form filaments, then the matrix material can be combined with fibrin and PEG and electrosprayed to form an electroprocessed fibrin-containing matrix. Once fibrin formation begins, a gel of the matrix material and fibrin together is produced.

Alternatively, the material can be sputtered with another molecule that forms a sheet. Examples of molecules that form sheets include PGA, PLA, a copolymer of PGA and PLA, collagen, and fibronectin. In some embodiments, a sheet is formed with two or more materials that can combine to form a third material. This sheet can be placed in a wet environment to allow conversion to the third material.

In addition to the multiple equipment variations and modifications that can be made to obtain desired results, similarly the electroprocessed solution can be varied to obtain different results. For instance, any solvent or liquid in which the material is dissolved, suspended, or otherwise combined without deleterious effect on the process or the safe use of the matrix can be used. Materials or the compounds that form materials can be mixed with other molecules, monomers or polymers to obtained desired results. In some embodiments, polymers are added to modify the viscosity of the solution. In still a further variation, when multiple reservoirs are used, the ingredients in those reservoirs are electrosprayed separately or joined at the nozzle so that the ingredients in the various reservoirs can react with each other simultaneously with the streaming of the solution into the electric field. Also, when multiple reservoirs are used, the different ingredients in different reservoirs can be phased in temporally during the processing period. These ingredients may include substances.

Embodiments involving alterations to the electroprocessed materials themselves are within the scope of the present invention. Some materials can be directly altered, for example, by altering their carbohydrate profile. Also, other materials can be attached to the matrix materials before, during or after electroprocessing using known techniques such as chemical cross-linking or through specific binding interactions (e.g. PDGF binds to collagen at a specific binding site). Further, the temperature and other physical properties of the process can be modified to obtain different results. The matrix may be compressed or stretched to produce novel material properties.

Still further chemical variations are possible. Fibrin, for example, is formed in different ways. Building an electroprocessed matrix comprised of fibrin, therefore, involves different ways of bringing the molecules capable of forming fibrin, such as fibrinogen and thrombin, together through electroprocessing methods. Electroprocessed materials and matrices can also be manipulated after they are formed with the electroprocessing methods.

A matrix of electroprocessed fibers, in accordance with the present invention, can be produced as described below. In the case of electrospun fibrin, while any molecules capable of forming fibrin can be used, it is preferable to electroprocess fibrinogen or thrombin to make fibrin fibers.

Electroprocessing using multiple jets of different polymer solutions and/or the same solutions with different types and amounts of substances (e.g., growth factors) can be used to prepare libraries of biomaterials for rapid screening. Such libraries are desired by those in the pharmaceutical, advanced materials and catalyst industries using combinatorial synthesis techniques for the rapid preparation of large numbers (e.g., libraries) of compounds that can be screened. For example, the minimum amount of growth factor to be released and the optimal release rate from a fibrous polymer scaffold to promote the differentiation of a certain type of cell can be investigated using the compositions and methods of the present invention. Other variables include fiber diameter and fiber composition. Electroprocessing permits access to an array of samples on which cells can be cultured in parallel and studied to determine selected compositions which serve as promising cell growth substrates.

Various effective conditions can be used to electroprocess a matrix. While the following is a description of a preferred method, other protocols can be followed to achieve the same result. Referring to FIG. 1 in electrospinning fibers, micropipettes 10 are filled with materials and suspended above a grounded target 11, for instance, a metal ground screen placed inside the central cylinder of the RCCS bioreactor. Although this embodiment involves two micropipettes acting as sources of materials, the present invention includes embodiments involving only one source or more than two sources. A fine wire 12 is placed in the solution to charge the solution in each pipette tip 13 to a high voltage. At a specific voltage determined for each solution and apparatus arrangement, the solution suspended in each pipette tip is directed towards the grounded target. This stream 14 of materials may form a continuous filament, for example when collagen is the material, that upon reaching the grounded target, collects and dries to form a three-dimensional, ultra thin, interconnected matrix of electroprocessed collagen fibers. Depending upon reaction conditions a single continuous filament may be formed and deposited in a non-woven matrix.

Figure 2:
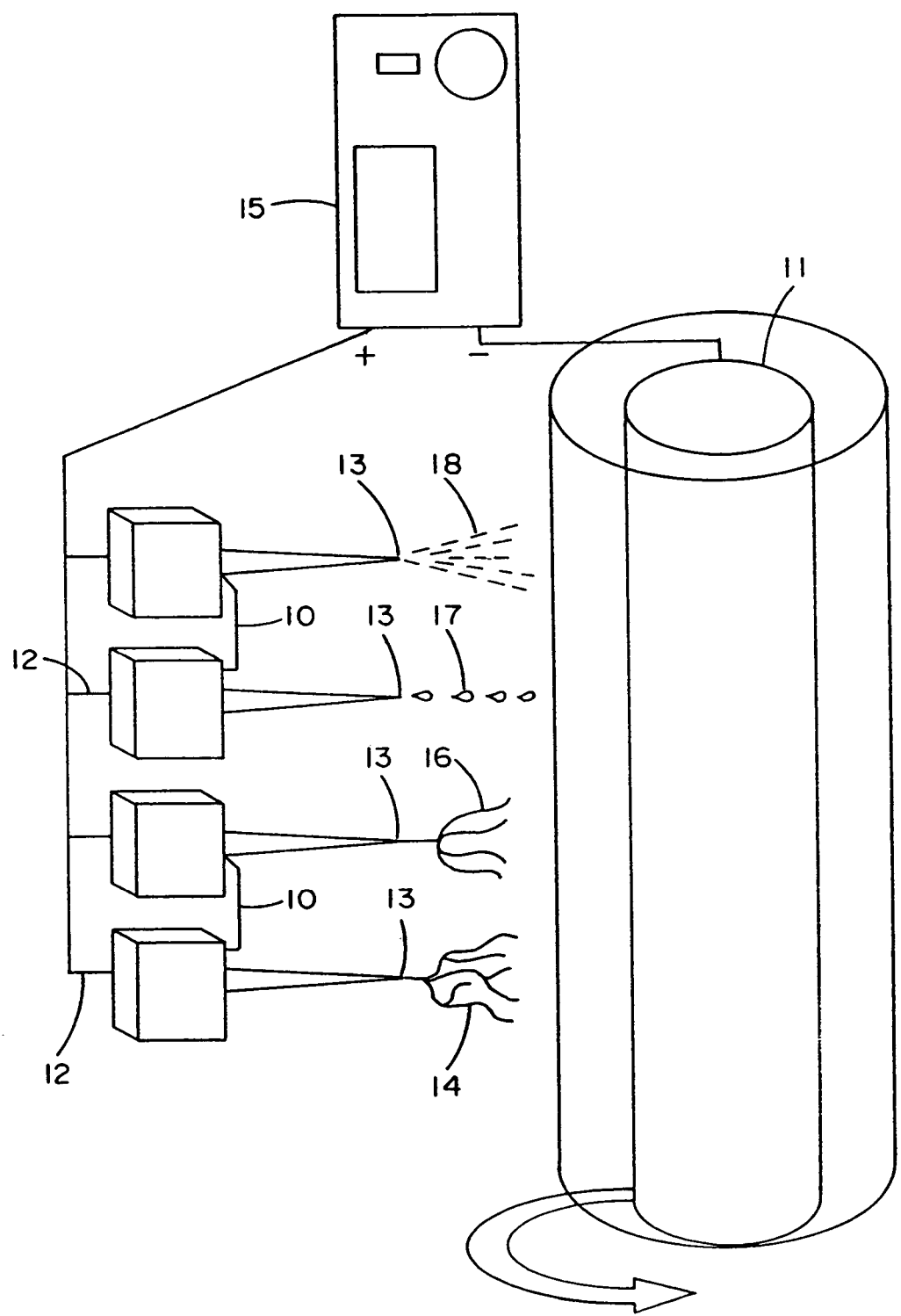
FIG. 2 is a schematic drawing of an embodiment of an electroprocessing device including the electroprocessing equipment and a rotating wall bioreactor.

As noted above, combinations of electroprocessing techniques and substances are used in some embodiments. Referring now to FIG. 2, micropipette tips 13 are each connected to micropippettes 10 that contain different materials or substances. The micropipettes are suspended above a grounded target 11. Again, fine wires 12 are used to charge the solutions. One micropipette produces a stream of collagen fibers 14. Another micropipette produces a steam of electrospun PLA fibers 16. A third micropipette produces an electroaerosol of cells 17. A fourth micropipette produces an electrospray of PLA droplets 18. Although the micropipettes are attached to the same voltage supply 15, PLA is electrosprayed rather than electrospun from the fourth micropipette due to variation in the concentration of PLA in the solutions. Alternatively, separate voltage supplies (not shown) can be attached to each micropipette to allow varying electroprocessing methods to be used through application of different voltage potentials.

Figure 8:
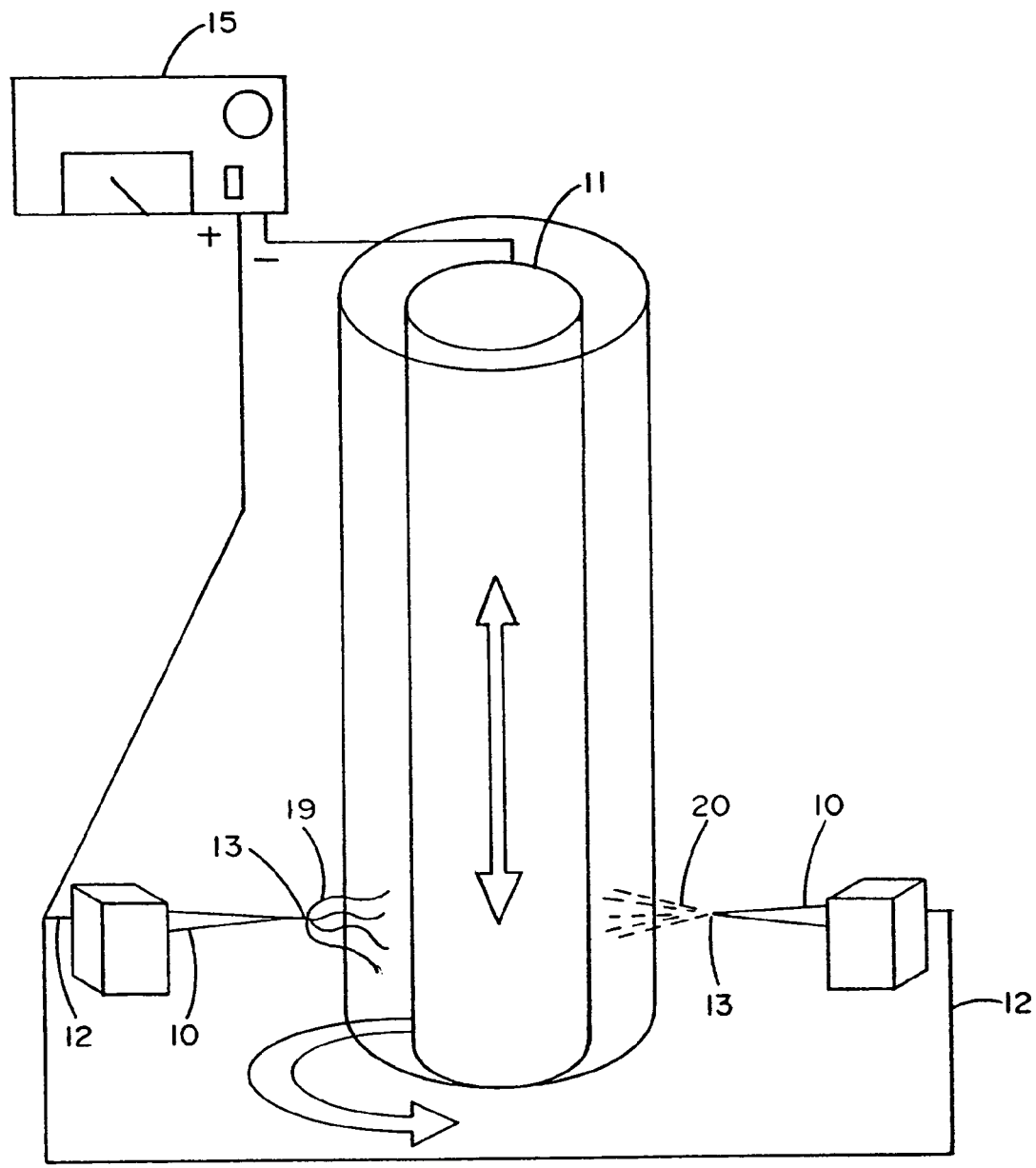
FIG. 8 is a schematic drawing of another embodiment of an electroprocessing device including the electroprocessing equipment and a rotating wall bioreactor.

Similarly, referring now to FIG. 8, the same material can be applied as electrospun fibers 19 from one of the two micropipettes and electrosprayed droplets 20 from the other micropipette disposed at a different angles with respect to the grounded substrate 11. Again, the micropipette tips 13 are attached to micropipettes 10 that contain varying concentrations of materials and thus produce different types of electroprocessed streams despite using the same voltage supply 15 through fine wires 12.

Minimal electrical current is involved in this process, and, therefore, electroprocessing, in this case electrospinning, does not denature the materials that form the electroprocessed materials, because the current causes little or no temperature increase in the solutions during the procedure. In melt electrospinning, there is some temperature increase associated with the melting of the material. In such embodiments, care is exercised to assure that the materials or substances are not exposed to temperatures that will denature or otherwise damage or injure them.

An electroaerosoling process can be used to produce a dense, matte-like matrix of electroprocessed droplets of material. The electroaerosoling process is a modification of the electrospinning process in that the electroaerosol process utilizes a lower concentration of matrix materials or molecules that form electroprocessed materials during the procedure. Instead of producing a splay of fibers or a single filament at the charge tip of the nozzle, small droplets are formed. These droplets then travel from the charged tip to the grounded substrate to form a sponge-like matrix composed of fused droplets. In some embodiments, the droplets are less than 10 microns in diameter. In other embodiments a construct composed of fibrils with droplets, like "beads on a string" may be produced. Droplets may range in size from 100 nanometers to 10 microns depending on the polymer and solvents.

As with the electrospinning process described earlier, the electroaerosol process can be carried out using various effective conditions. The same apparatus that is used in the electrospinning process, for instance as shown in FIG. 1, is utilized in the electroaerosol process. The differences from electrospinning include the concentration of the materials or substances that form matrix materials placed in solution in the micropipette reservoir and/or the voltage used to create the stream of droplets.

One of ordinary skill in the art recognizes that changes in the concentration of materials or substances in the solutions requires modification of the specific voltages to obtain the formation and streaming of droplets from the tip of a pipette.

The electroprocessing process can be manipulated to meet the specific requirements for any given application of the electroprocessed compositions made with these methods. In one embodiment, the micropipettes can be mounted on a frame that moves in the x, y and z planes with respect to the grounded substrate. The micropipettes can be mounted around a grounded substrate, for instance a tubular mandrel.

In this way, the materials or molecules that form materials streamed from the micropipettes can be specifically aimed or patterned. Although the micropipettes can be moved manually, the frame onto which the micropipettes are mounted is preferably controlled by a microprocessor and a motor that allow the pattern of streaming collagen to be predetermined by a person making a specific matrix. Such microprocessors and motors are known to one of ordinary skill in the art. For instance, matrix fibers or droplets can be oriented in a specific direction, they can be layered, or they can be programmed to be completely random and not oriented.

In the electrospinning process, the stream or streams can branch out to form fibers. The degree of branching can be varied by many factors including, but not limited to, voltage, ground geometry, distance from micropipette tip to the substrate, diameter of micropipette tip, and concentration of materials or compounds that will form the electroprocessed materials. As noted, not all reaction conditions and polymers may produce a true multifilament, under some conditions a single continuous filament is produced. Materials and various combinations can also be delivered to the electric field of the system by injecting the materials into the field from a device that will cause them to aerosol. This process can be varied by many factors including, but not limited to, voltage (for example ranging from about 0 to 30,000 volts), distance from micropipette tip to the substrate (for example from 0-40 cm), the relative position of the micropipette tip and target (i.e. above, below, aside etc.), and the diameter of micropipette tip (approximately 0-2 mm). Several of these variables are well known to those of skill in the art of electrospinning microfiber textile fabrics.

The geometry of the grounded target can be modified to produce a desired matrix. By varying the ground geometry, for instance having a planar or linear or multiple points ground, the direction of the streaming materials can be varied and customized to a particular application. For instance, a grounded target comprising a series of parallel lines can be used to orient electrospun materials in a specific direction. The grounded target can be a cylindrical mandrel whereby a tubular matrix is formed. Most preferably, the ground is a variable surface that can be controlled by a microprocessor that dictates a specific ground geometry that is programmed into it. Alternatively, for instance, the ground can be mounted on a frame that moves in the x, y, and z planes with respect to a stationary micropipette tip streaming collagen.

The substrate onto which the materials are streamed, sprayed or sputtered can be the grounded target itself or it can be placed between the micropipette tip and the grounded target. The substrate can be specifically shaped, for instance in the shape of a nerve guide, skin patch, fascial sheath, or a vascular graft for subsequent use in vivo. The electroprocessed compositions can be shaped to fit a defect or site to be filled. Examples include a site from which a tumor has been removed, an injury site in the skin (a cut, a biopsy site, a hole or other defect) and a missing or shattered piece of bone. The electroprocessed compositions may be shaped into shapes useful for substance delivery, for example, a skin patch, a lozenge for ingestion, an intraperitoneal implant, a subdermal implant, the interior lining of a stent, a cardiovascular valve, a tendon, a ligament a dental prosthesis, a muscle implant, or a nerve guide. Electroprocessing allows great flexibility and allows for customizing the construct to virtually any shape needed. Many matrices are sufficiently flexible to allow them to be formed to virtually any shape. In shaping matrices, portions of the matrix may be sealed to one another by, for example, heat sealing, chemical sealing, and application of mechanical pressure or a combination thereof. An example of heat sealing is the use of crosslinking techniques discussed herein to form crosslinking between two portions of the matrix. Sealing may also be used to close an opening in a shaped matrix. Suturing may also be used to attach portions of matrices to one another or to close an opening in a matrix. It has been observed that inclusion of synthetic polymers enhances the ability of matrices to be heat sealed.

Other variations of electroprocessing, particularly electrospinning and electroaerosoling include, but are not limited to the following:

1. Using different solutions to produce two or more different fibers or droplets simultaneously (fiber or droplet array). In this case, the single component solutions can be maintained in separate reservoirs.

2. Using mixed solutions (for example, materials along with substances such as cells, growth factors, or both) in the same reservoir(s) to produce fibers or droplets composed of electroprocessed materials as well as one or more substances (fiber composition "blends"). Nonbiological but biologically compatible material can be mixed with a biological molecule.

3. Utilizing multiple potentials applied for the different solutions or the same solutions.

4. Providing two or more geometrically different grounded targets (i.e. small and large mesh screens).

5. Placing the mold or mandrel or other ungrounded target in front of the grounded target.

6. Applying agents such as Teflon onto the target to facilitate the removal of electroprocessed materials from the target (i.e. make the material more slippery so that the electroprocessed materials do not stick to the target).

7. Forming an electroprocessed material that includes materials applied using multiple electroprocessing methods. For example, electrospun fibers and electroaerosol droplets in the same composition can be beneficial for some applications depending on the particular structure desired. This combination of fibers and droplets can be obtained by using the same micropipette and solution and varying the electrical charge; varying the distance from the grounded substrate; varying the polymer concentration in the reservoir; using multiple micropipettes, some for streaming fibers and others for streaming droplets; or any other variations to the method envisioned by those of skill in this art. The fibers and droplets can be layered or mixed together in same layers. In applications involving multiple micropipettes, the micropipettes can be disposed in the same or different directions and distances with reference to the target.

8. Using multiple targets.

All these variations can be done separately or in combination to produce a wide variety of electroprocessed materials and substances.

The various properties of the electroprocessed materials can be adjusted in accordance with the needs and specifications of the cells to be suspended and grown within them. The porosity, for instance, can be varied in accordance with the method of making the electroprocessed materials or matrix. Electroprocessing a particular matrix, for instance, can be varied by fiber (droplet) size and density. If the cells to be grown in the matrix require a great deal of nutrient flow and waste expulsion, then a loose matrix can be created. On the other hand, if the tissue to be made requires a very dense environment, then a dense matrix can be designed. Porosity can be manipulated by mixing salts or other extractable agents. Removing the salt will leave holes of defined sizes in the matrix.

One embodiment for appropriate conditions for electroprocessing fibrin is presented below. For electroprocessing fibrin by combining fibrinogen and thrombin, the appropriate approximate ranges are: voltage 0-30,000 volts; pH 7.0 to 7.4; calcium 3 to 10 mM; temperature 20 to 40° C.; ionic strength 0.12 to 0.20 M; thrombin 0.1 to 1.0 units per ml; and fibrinogen 5 to 25 mg/ml. For electroprocessing fibrin monomer, the pH starts at 5 and increases to 7.4 while the ionic strength starts above 0.3 M and decreases to 0.1 M. The other conditions are similar as stated within this paragraph. Electroprocessed fibrin matrices of varying properties can be engineered by shifting the pH, changing the ionic strength, altering the calcium concentration, or adding additional polymeric substrates or cationic materials. For electroprocessing collagen, the appropriate approximate ranges are: voltage 0-30,000 volts; pH 7.0 to 8.0; temperature 20 to 42° C.; and collagen 0 to 5 mg/ml. Electroprocessed collagen matrices of varying properties can be engineered by shifting the pH, changing the ionic strength (e.g. addition of organic salts), or adding additional polymeric substrates or cationic materials.

Shapes of Electroprocessed Materials and Matrices

Electroprocessed materials can be electrodeposited inside a specifically shaped mold. For instance, a particular type of organ or tissue that to be replaced has a specific shape, such as a skinpatch to fit a biopsy site or a large scalp area following a wide area removed after discovering a malignant melanoma. That shape is then reproduced and created inside a mold designed to mimic that shape. This mold can be filled by electrodepositing the material into it. In this way, the matrix exactly mimics the mold shape. In some embodiments, matrices that will become extracellular matrices and that have a specific shape are used in the creation of a new organ. Hollow and solid organs can be made. Mixing cells with the material during electrospraying forms cells within the matrix so that they do not have to migrate into a matrix.

Methods of Combining Substances with Electroprocessed Materials

Substances can be combined with the electroprocessed materials by a variety of means. In some embodiments, the substance comprises molecules to be released from the electroprocessed material and is therefore added to or incorporated within the matrix of electroprocessed material. Substances can be mixed in the solvent carriers or solutions of materials for electroprocessing. In this system materials can be mixed with various substances and directly electroprocessed. The resulting composition comprising an electroprocessed matrix and substance can be topically applied to a specific site and the substances released from the material as a function of the material undergoing breakdown in the surrounding environment. Substances may also be released from the electroprocessed compositions of the present invention through diffusion.

The state of the electroprocessed material in relation to the incorporated substances is dictated and can be controlled by the chemistry of the system and varies based on the selection of matrix materials, solvent(s) used, and solubility of the matrix materials in those solvents. These parameters can be manipulated to control the release of the substances (or other elements into the surrounding environment). If substances to be incorporated into the electroprocessed material are not miscible with the material, separate solvent reservoirs for the different components can be used. Mixing in such an embodiment occurs prior to, during, and/or after deposition on the target, or a combination thereof. It is to be understood that substances may be entrapped or entangled within an electroprocessed material, bonded to a material before the material undergoes electroprocessing, or bound to specific sites within the matrix material.

In a variation of this embodiment, the substance is a particle or aggregate comprising a matrix of compounds or polymers such as alginate that, in turn, contain one or more compounds that will be released from the electroprocessed material. Drugs can be combined with alginate by, for example, combining a drug suspension or drug particulate in the alginate in the presence of calcium. Alginate is a carbohydrate that forms aggregates when exposed to calcium. the aggregates can be used to trap drugs. The aggregates dissolve over time, releasing the trapped substances, such as cells trapped in alginate. The particles, which are then incorporated within the larger electroprocessed matrix, are biologically compatible but relatively stable and will degrade gradually. In some circumstances, the electroprocessed materials resemble a string of pearls. This is a physical aspect of the electroprocessing. If the polymer concentration is low, electrospraying of beads occurs. As polymer concentration increases there are some beads and some fibers. A further increase in polymer concentration leads to predominantly or all fibers. Therefore, the appearance of the pearls on a string is a transition phase.

If a drug (for example, penicillin) does not bind or interact with an electrospun matrix material, the drug can be entrapped in PGA or PLA pellets or electroaerosoled to produce pellets in the electrospun material. The pellets or electroaerosoled droplets containing the drug begin to dissolve after administration to deliver the entrapped material. Some agents can be coupled to synthetic, or natural polymer by a covalent bond, prior to or after spinning.

In other embodiments, the substance is electroprocessed. Substances can be electroprocessed from the same orifice as the materials or from different orifices. Substances can also be subjected to the same or a different type of electroprocessing as the material. A molecule can be bonded to the electroprocessed material directly or through linking to a molecule that has an affinity for the material. An example of this embodiment involves bonding polypeptide substances to heparin, which has an affinity for collagen materials. This embodiment allows release relate to be controlled by controlling the rate of degradation of the material, for example by enzymatic or hydrolytic breakdown.

In other embodiments, the electroprocessed material can entrap substance during the electrodeposition process. This can be accomplished by disposing substances in the space between the source of the electroprocessed stream and the target for the electroprocessed material. Placing such substances in the space between the source and target can be accomplished by a number of methods, including but not limited to, suspending in air or other gases, dripping, spraying, or electroprocessing the substances. The substances can be present in that space in, for example, particulate, aerosol, colloidal, or vapor form. In these embodiments, the electroprocessed material or matrix will physically entrap the substances. This embodiment can also be used to encapsulate larger particles, such as cells, large particles, or tablets. For example, if a tablet is dropped through the matrix as it forms, the tablet is surrounded by the matrix. If a small object, like a cell is dropped through the matrix as it forms or placed in an aerosol within the matrix, the object may be trapped between filaments, within filaments or "attached to the outside of the filaments. For example, by suspending cells in a solution or within a matrix, the cells can become part of an electrospun matrix during fabrication of the filaments. Alternatively, encapsulation can occur by dropping substances onto or through a matrix material stream as a matrix forms. The cells thus become surrounded by a matrix of electroprocessed material. These embodiments can be used to incorporate within a matrix substances that are not soluble and/or are too large to form a suspension in the solvent used for the production of the material. For substances in a mist or vapor form, controlling distribution and composition of substances in the space between the source and target can be used to alter the physical and chemical properties of the electroprocessed material and the pattern of distribution of the substances in the electroprocessed material. For all of the foregoing embodiments, the substances can be placed in the electroprocessed material in capsules, vesicles, or other containments for subsequent release. Since the solvent carrier often evaporates in the electroprocessing technique as the electroprocessed material forms, such as a filament, substances may be placed in the electroprocessed matrix and solvent toxicity is greatly reduced or eliminated.

In embodiments wherein the substance comprises cells, the cells can, for example, be suspended in a solution or other liquid that contains the material to be electroprocessed, disposed in the area between the solutions and target, or delivered to a target or substrate from a separate source before, during, or after electroprocessing. Cells can be dripped through the matrix, onto the matrix as it deposits on the target or suspended within an aerosol as a delivery system for the cells to the electroprocessed material. The cells can be delivered in this manner while the matrix is being formed. As an example, cardiac fibroblasts were suspended in phosphate-buffered saline (PBS) at a concentration of approximately one million cells per milliliter. The suspension of cells was placed within a reservoir of a Paasche air brush. To test the efficacy of using this type of device to deliver cells, the cell suspension was initially sprayed onto a 100 mm culture dish. Some of the cells survived, attached to the dish and spread out over the substratum. In a second trial, the culture dish was located further away from the air brush and the experiment was repeated. Cells were observed on the dish. They appeared to be flattened by the impact and were partially spread out over the surface of the substratum. Culture media was added to the dish and the cells were placed into an incubator. After one hour of culture, the cells were inspected again, and many were found to have spread out further over the substratum. These results demonstrate that a simple airbrush device can be used to place cells into an aerosol droplet and deliver them on demand to a surface or site of interest. Cell viability can be improved by restricting this technique to cells that are resistant to the shear forces produced in the technique, developing a cell suspension with additives that cushions the cells or refining the aerosolizing device to produce a more laminar flow. In addition, directing the cell aerosol into matrix materials as the matrix is forming in the space between the target or mandrel and the source(s) of molecules being electroprocessed produces the effect of cushioning the cells. While not wanting to be bound by the following statement, it is believed that the cells will be trapped in the storm of filaments or other bodies produced by electrospinning or electroprocessing and pulled onto the mandrel. This situation may be less traumatic to the cells than directly spraying the cells onto a solid surface.

In one embodiment, the cells are added either before or at the same time as the materials or compounds that form electroprocessed materials are brought together. In this way, the cells are suspended throughout the three-dimensional matrix. In embodiments in which the electroprocessed material comprises fibrin formed by combining thrombin and fibrinogen, the cells are typically included in the mixture that contains the fibrinogen (whether it is plasma or purified fibrinogen). Whenever materials comprise two or more separate materials that combine to form a different material (such as fibrinogen and thrombin) bringing the materials together immediately prior to insertion into a mold, or immediately prior to the streaming step in the electrospinning process helps result in a good distribution of cells in suspension in the resulting extracellular matrix.

Cells can be added as the filaments are produced in the space between the target and polymer source. This is accomplished by dripping the cells onto the target, dripping the cells into the matrix as it forms, aerosoling the cells into the matrix or onto the target or electrospraying the cells into the matrix as it condenses and forms near or on the grounded target. In another embodiment, cells are sprayed or dribbled into a forming electroprocessed material or matrix and thereby trapped as the electroprocessed material crosses the air gap between the source solutions and target.

An alternative method to deliver cells to an electroprocessed material involves electroaerosol delivery of the cells. Cells can be deposited by electrostatic spraying at, for example, 8 kV directly onto standard polystyrene culture dishes, suggesting that electrostatic cell spraying is a viable approach. Cardiac fibroblasts in phosphate buffered saline (PBS) have been electroaerosoled up to a 20 Kv potential difference. In another example, Schwann cells (rat) were plated on a PS petri dish by conventional methods after one day. Schwann cells were also electrosprayed onto a PS petri dish with a metal ground plate behind the dish at 10 kV after one day. Both samples grew to almost confluence after one week. The electroaerosol approach provides some distinct advantages. First, the shear forces produced during the delivery phase (i.e. the production of the aerosol) appear to be much less traumatic to the cells. Second, the direction of the aerosol can be controlled with a high degree of fidelity. In essence the cell aerosol can be painted onto the surface of interest. This allows the cell to be targeted to specific sites. In electroaerosol delivery, cells are suspended in an appropriate media (e.g. culture media, physiological salts, etc.) and charged to a voltage, and directed towards a grounded target. This process is very similar to that used in electroprocessing, particularly electrospinning. The produces a fine mist of cells trapped within the droplets as they are produced and directed at the grounded target.

Cells can be delivered using aerosol and electroaerosol techniques onto an electroprocessed material that is forming by an electroprocessing technique. The electroaerosol of cells can be delivered in parallel (i.e. alongside) the electroprocessing material or from a separate site. The cells can be delivered to the storm of filaments or particles produced within the air gap in the electrodeposition process or directed at the target. The cells and electroprocessed material also can be delivered in an alternating sequence to the target, i.e. electrodeposit the material, aerosol the cells, electrodeposit the material, aerosol the cells. This allows for the discrete layering of the construct in separate layers. Furthermore, a vapor source can be provided that directs water onto the mandrel of target used to collect the cells. Providing this moisture improves cell viability by keeping the cells from dehydrating during processing. Cells can be added to the electroprocessed material at any time or from any orientation in any aerosol strategy. Again the advantage of the process in general is that collagen, for example, collects in a dried state on the target mandrel. Accordingly, although some solvents for collagen may be toxic, they. are lost from the system before the filaments collect on the target.

Cells can also be trapped within a carrier prior to producing an aerosol. For example, cells can be encapsulated within a material like alginate. The encapsulated cells are physically protected from shear and trauma during processing. Cells delivered in this form to the electroprocessed material will have higher viability when sprayed or electrostatically seeded.

An electroaerosol or otherwise electroprocessed material can also be delivered directly to an in situ site. For example, an electroprocessed material can be produced directly onto a skin wound, with or without substances such as molecules or cells. Additional cells or materials can then be aerosolized onto or into the wound site. Other surgical sites can also be amenable the delivery of materials using various electrodeposition techniques or combinations thereof of these methods.

In other embodiments, substances can be applied to the electroprocessed material after formation, for example by soaking the electroprocessed material in the substance or by spraying the substance onto the electroprocessed material.

Persons skilled in the art will recognize that more than one method for combining the substances with electroprocessed materials can be used in a single embodiment or application. Combining methods can be especially useful in embodiments involving release of more than one compound or compounds intended to have complex release kinetics, although such combinations are not limited to those embodiments.

Magnetically and electrically active materials can be electroprocessed, including, for example, preparing conducting polymer fibers produced by electrospinning. In addition, conducting polymers can be prepared in-situ in the matrix by, for example, incorporation of a monomer (e.g., pyrrole) followed by treatment with polymerization initiator and oxidant (e.g., $FeCl_3$). Finally, conducting polymers can be grown in the material after electroprocessing by using a matrix-coated conductor as the anode for electrochemical synthesis of, for example, polypyrrole or polyaniline. Compounds that can form electroprocessed materials can be added to an aqueous solution of pyrrole or aniline to create a conducting polymer at the anode with the entrapped electroprocessed material-forming compounds, which can then be treated with other compounds to allow formation of the material to occur.

Patterns of Electroprocessed Materials and Substance Distribution

Many embodiments of the present invention involve means for manipulating the pattern or distribution of electroprocessed materials and/or substances within an electroprocessed material. For example, an electroprocessing target can also be specifically charged or grounded along a preselected pattern so that electroprocessed materials streamed toward the target are directed into specific directions or distributions on the target or on a substrate. The electric field can be controlled by a microprocessor to create a matrix having a desired geometry. The target and the electroprocessing nozzle or nozzles can be movable with respect to each other and to the target thereby allowing additional control over the geometry of the electroprocessed material to be formed. In embodiments in which substances are electroprocessed, this manipulation will also allow control of the distribution of substances within the electroprocessed materials. For example a matrix can be prepared on a mandrel, and substances from a separate reservoir can be sprayed, dripped, electroprocessed in a specific pattern over the existing matrix. This may also be accomplished by simultaneously electrospraying a matrix from one source and a substance from another source. In this example the matrix source may be stationary and the substance source is moved with respect to the target mandrel.

Other features that allow establishment of such a pattern include, but are not limited to, the ability to deposit multiple layers of the same or different materials, combining different electroprocessing methods, the use multiple orifices with different contents for electroprocessing, and the existence of numerous methods for combining substances with the materials. For example, a gradient of substances can be created along a electroprocessed material. In embodiments in which the matrix is shaped into a cylindrical construct, for example, the gradient can be prepared along the long axis of a construct (left to right) or the perpendicular axis (inside to out). This configuration is used to provide a chemoattractant gradient to guide the movement of cells within a specified site. Thus, for example, in some embodiments in which neovascular agents are prepared in a perpendicular gradient along a collagen-based construct, the agents can be concentrated on the dorsal surface of a sheet of the material. The ventral side can be placed against a wound and the higher concentration of angiogenic materials on the dorsal surface of the construct will increase the migration of endothelial cells through the electrospun material. Again, embodiments with complex patterns can use a microprocessor programmed with the specific parameters to obtain a specific, preselected electroprocessed pattern of one or more electroprocessed polymers, optionally with one or more substances.

Uses for the Compositions of the Present Invention

Substance Delivery

One use of the compositions of the present invention is the delivery of one or more substances to a desired location. In some embodiments, the electroprocessed materials are used simply to deliver the materials itself. In other embodiments, the electroprocessed materials are used to deliver substances that are contained in the electroprocessed material or that are produced or released by substances contained in the electroprocessed material. For example, an electroprocessed material containing cells can be implanted in a body and used to deliver molecules produced by the cells after implantation. The present compositions can be used to deliver substances to an in vivo location, an in vitro location, or other locations. The present compositions can be administered to these locations using any method.

In the field of substance delivery, the compositions of the present invention have many attributes that allow delivery of substances using a wide variety of release profiles and release kinetics. For example, selection of the substance and the method by which the substance is combined with the electroprocessed material affects the substance release profile. To the extent that the substances are not immobilized by the electroprocessed material, release from the electroprocessed material is a function of diffusion. An example of such an embodiment is one in which the substance is sprayed onto the electroprocessed material. To the extent that the substances are immobilized by the electroprocessed material, release rate is more closely related to the rate at which the electroprocessed material degrades. An example of such an embodiment is one in which the substance is covalently bonded to the electroprocessed material. For a substance is trapped within an electrospun aggregate or filament, release kinetics would be determined by the rate at which the surrounding material degrades or disintegrates. Still other examples are substances that are coupled to the electroprocessed material by a light sensitive bond. Exposing such a bond to light releases the substance from the electroprocessed material. Conversely, in some embodiments of this invention, materials can be exposed to light to cause binding of agents in vivo or in vitro. Combining the compound with the electroprocessed material in solution, rather than in suspension, will result in a different pattern of release and thereby provide yet another level of control for the process. Further, the porosity of the electroprocessed material can be regulated, which affects the rate of release of a substance. Enhanced porosity facilitates release. Substance release is also enhanced by fragmenting or pulverizing the electroprocessed material. Pulverized material can, for example be applied to a wound site, ingested or formed into another shape such as a capsule or a tablet. In embodiments in which the substance is present in the form of a large-particle such as a tablet encapsulated in the electroprocessed material or a molecule trapped inside an electroprocessed filament, release is dictated by a complex interplay of the rate the particles dissolve or degrade and any breakdown or degradation of the electroprocessed material structure. In embodiments in which the substance comprises cells that will express one or more desired compounds, factors that affect the function and viability of the cells and the timing, intensity, and duration of expression can all affect the release kinetics. Chemicals that affect cell function, such as oligonucleotides, promoters or inhibitors of cell adhesion, hormones, and growth factors, for example, can be incorporated into the electroprocessed material and the release of those substances from the electroprocessed material can provide a means of controlling expression or other functions of cells in the electroprocessed material.

Release kinetics in some embodiments are manipulated by cross-linking electroprocessed material through any means. In some embodiments, crosslinking will alter, for example, the rate at which the electroprocessed material degrades or the rate at which a compound is released from the electroprocessed material by increasing structural rigidity and delaying subsequent dissolution of the electroprocessed material. Electroprocessed materials can be formed in the presence of cross-linking agents or can be treated with cross-linking agents after electrodeposition. Any technique for cross-linking materials may be used as known to one of ordinary skill in the art Examples of techniques include application of cross-linking agents and application of certain cross-linking radiations. Examples of cross-linking agents that work with one or more proteins include but are not limited to condensing agents such as aldehydes e.g., glutaraldehyde, carbodiimide EDC (1-ethyl-3(3 dimethyl aminopropyl)), photosensitive materials that cross link upon exposure to specific wavelengths of light, osmium tetroxide, carbodiimide hydrochloride, and NHS (n-hydroxysuccinimide), and Factor XIIIa. Ultraviolet radiation is one example of radiation used to crosslink matrix materials in some embodiments. Natural materials can be cross-linked with other natural materials. For example, collagen can be cross-linked and or stabilized by the addition of fibronectin and or heparin sulfate. For some polymers heat can be used to alter the matrix and cross link elements of the matrix by fusing adjacent components of the construct. Polymers may also be partially solubilized to alter the structure of the material, for example brief exposure of some synthetics to alcohols or bases can partially dissolve and anneal adjacent filaments together. Some polymers may be cross-linked using chemical fusion or heat fusion techniques. Synthetic polymers generally can be cross-linked using high energy radiation (e.g., electron beams, gamma rays). These typically work by the creation of free radicals on the polymer backbone which then couple, affording cross links. Backbone free radicals can also be generated via peroxides, azo compounds, aryl ketones and other radical-producing compounds in the presence of heat or light. Reduction-oxidation reactions that produce radicals (e.g., peroxides in the presence of transition metal salts) can also be used. In many cases, functional groups on polymer backbones or side chains can be reacted to form cross-links. For example, polysaccharides can be treated with diacylchlorides to form diester cross-links. Cross-linking may also occur after application of a matrix where desirable. For example, a matrix applied to a wound may be cross-linked after application to enhance adhesion of the matrix to the wound.

The release kinetics of the substance is also controlled by manipulating the physical and chemical composition of the electroprocessed material. For example, small fibers of PGA are more susceptible to hydrolysis than larger diameter fibers of PGA. An agent delivered within an electroprocessed material composed of smaller PGA fibers is released more quickly than when prepared within a material composed of larger diameter PGA fibers.

In some embodiments substances such as peptides can be released in a controlled manner in a localized domain. Examples include embodiments in which the substance is chemically or covalently bonded to the electroprocessed material. The formation of peptide gradients is a critical regulatory component of many biological processes, for example in neovasculogenesis. In surgical applications, anti-vascular peptides or anti-sense oligonucleotides can be incorporated into an electroprocessed material that is then wrapped around or placed within a tumor that is inaccessible to conventional treatments to allow for localized release and effect. Release of the anti-vascular substances suppresses tumor growth. Antisense oligonucleotides can be released from the construct into the tumor and used to suppress the expression gene sequences of interest. In another example anti-sense sequences directed against gene sequences that control proliferation can be delivered within an electroprocessed matrix coated stent. The stretch normally associated with the placement of the stent initiates smooth muscle cell proliferation, and antisense sequences designed to suppress cell division reduce the deleterious effects of the smooth muscle cell proliferation associated with the procedure. In another embodiments, the electroprocessed material delivers sense and antisense oligonucleotides to promote or to inhibit localized cell function for a period of time. For example, an antisense oligonucleotide is released from an electroprocessed material to suppress the expression of a deleterious enzyme in a wound. Examples of such enzymes are matrix metalloproteinases (MMPs), which are often overexpressed in chronic wounds. In another example, the electroprocessed material applied to a wound releases plasmids that contain nucleotide sequences coding for tissue inhibitors of metalloproteinases (TIMPs). Cells in the wound will express TIMPs, resulting in local delivery of TIMPs that will inhibit MMP function.

Physical processing of the formed electroprocessed material is another way to manipulate release kinetics. In some embodiments, mechanical forces, such as compression, applied to an electroprocessed material hasten the breakdown of the matrix by altering the crystalline structure of the material. Structure of the matrix is thus another parameter that can be manipulated to affect release kinetics. Polyurethanes and other elastic materials such as poly(ethylene-covinyl acetate), silicones, and polydienes (e.g., polyisoprene), polycaprolactone, polyglycolic acid and related polymers are examples of materials whose release rate can be altered by mechanical strain.

Release kinetics can also be controlled by preparing laminates comprising layers of electroprocessed materials with different properties and substances. For example, layered structures composed of alternating electroprocessed materials can be prepared by sequentially electroprocessing different materials onto a target. The outer layers can, for example, be tailored to dissolve faster or slower than respect the inner layers. Multiple agents can be delivered by this method, optionally at different release rates. Layers can be tailored to provide a complex, multi-kinetic release profile of a single agent over time. Using combinations of the foregoing can provide for release of multiple substances released, each with a complex profile.

Suspending a substance in particles that are incorporated in the electroprocessed material provides another means for controlling release profile. Selection of the composition of these smaller particle matrices provides yet another way to control the release of compounds from the electroprocessed material. The release profile can be tailored by the composition of the material used in the process.

Embodiments also exist in which the substances are contained in liposomes or other vesicles in the electroprocessed matrix. Vesicles are prepared that will release one or more compounds when placed in fluids at a specific pH range, temperature range, or ionic concentration. Methods for preparing such vesicles are known to persons of skill in the art. The electroprocessed material can be delivered to a site of interest immediately or is stored either dry or at a pH at which release will not occur, and then delivered to a location containing liquids that have a pH at which release will occur. An example of this embodiment is an electroprocessed material containing vesicles that will release a desired compound at the pH of blood or other fluids released from a wound. The matrix is placed over a wound and releases fluids upon discharge of fluids from the wound.

Incorporating constituents that are magnetically sensitive or electrically sensitive into the electroprocessed material provides another means of controlling the release profile. A magnetic or electric field can then be subsequently applied to some or all of the matrix to alter the shape, porosity and/or density of the electroprocessed material. For example, a field can stimulate movement or conformational changes in the matrix due to the movement of magnetically or electrically sensitive particles. Such movement can affect the release of compounds from the electroprocessed material. For example, altering the conformation of the material can increase or decrease the extent to which the material is favorable for compound release.

In some embodiments, magnetic or electrically sensitive constituents that have been processed or co-processed with an electroprocessed material can be implanted subdermally to allow delivery of a drug over a long interval of time. By passing a magnetic field or an electrical field across the material, drug release is induced. The electroprocessed material structure is stable and does not substantially change without electromagnetic stimulation. Such embodiments provide controlled drug delivery over a long period of time. For example, an electroprocessed material that has magnetic or electrical properties and insulin can be fabricated and placed subdermally in an inconspicuous site. By passing a magnetic field or an electrical field across the composition, insulin release can be induced. A similar strategy may be used to release compounds from a construct that has light sensitive elements, exposing these materials to light will either cause the material itself to breakdown and or cause the release of substances that are bound to the electroprocessed material by the light sensitive moiety.

In other embodiments, the substances comprise vesicles encapsulated within the electroprocessed material along with electrical or magnetic materials. The vesicles contain a compound to be released from the vesicles. Placing an electrical or magnetic field across the electroprocessed material causes the compounds within the vesicles can be released by, for example, deforming the vesicles to the point of rupture or by changing the permeability (in some cases reversibly) of the vesicle wall. Examples of these embodiments include transfection agents, such as liposomes, that contain nucleic acids that enhance the efficiency of the process of gene delivery to the cell.

In other embodiments, the composition comprising an electroprocessed material and substance is used as a transdermal patch for localized delivery of medication, or of a component of such a patch. In some of these embodiments, electrically conductive materials are incorporated into such a composition, which is then used as a component of an iontophoresis system in which one or more substances is delivered in response to the passage of electric current. Electrically conductive materials can have a direct healing effect on bone injuries. For example placing a small electric current across a fracture site promotes healing. An electroprocessed bone mimetic that conducts or produces current can be made and placed within a fracture. The addition of the electrical current will promote healing at a rate that is faster than the addition of the electroprocessed composition alone.

In other embodiments, an electroprocessed material or a portion thereof containing electromagnetic properties is stimulated by exposure to a magnet to move and thereby to apply or to release physical pressure to a pressure-sensitive capsule or other enclosure that contains molecules to be released from the material. Depending on the embodiment, the movement will affect the release relate of the encapsulated molecules.

Response of the composition to electric and magnetic fields can be regulated by features such as the composition of the electroprocessed material, size of the filaments, and the amount of conductive material added. Electromechanical response from polyaniline is the result of doping-induced volume changes, whereas ion gradients leading osmotic pressure gradients are responsible for field-induced deformation in ionic gels such as poly(2-acrylamido-2-methyl propanesulfonicacid). In each case, ion transport kinetics dominates the response, and facile transport is observed with the small fibers. Gel swelling and shrinking kinetics have been shown to be proportional to the square of the diameter of a gel fiber. Electromechanical response times of fiber bundles of less than 0.1 s, are possible in the regime of typical muscle.

Embodiments involving delivery of molecules produced by cells provide many means by which rejection and immune response to cells can be avoided. Embodiments using cells from a recipient thus avoid the problems associated with rejection and inflammatory and immunological response to the cells. In embodiments in which cells from an organism other than the recipient are used, the matrix can sequester the cells from immune surveillance by the recipient's immune system. By controlling parameters such as the pore size of the electroprocessed material or matrix, nutritive support to the cells trapped in the matrix can be permitted while the cells are protected from detection and response by the recipient's immune system. As an example, pancreatic islet cells that manufacture insulin collected from a donor can be encapsulated in an electroprocessed matrix and implanted in a recipient who cannot make insulin. Such an implant can be placed, for example, subdermally, within the liver, or intramuscularly. For some immune responses permanent sequestration from the host system may not be necessary. The electroprocessed material can be designed to shield the implanted material for a given length of time and then begin to breakdown. In still other embodiments, bacteria or other microbial agents engineered to manufacture the desired compound can be used. This embodiment provides the advantages of using cells that are more easily manipulated than cells from the recipient or a donor. Again, the electroprocessed material can serve to shield the bacteria from immune response in this embodiment. The advantage of using a bacteria carrier is that these microbes are more easily manipulated to express a wide variety of products. Embodiments in which cells are transiently transfected allow for expression to be limited to a defined period. Transient genetic engineering allows cells to revert to their original state in embodiments in which such reversion is desired to minimize the risks of complications.

In some embodiments, cells are genetically engineered such that the expression of a specific gene may be promoted or inhibited through various means known in the art. For example, a tetracycline sensitive promoter can be engineered into a gene sequence. That sequence is not expressed until the tetracycline is present. Cell markers or bacterial markers can also be used to identify the inserted material. For example, green fluorescent proteins placed within an engineered genetic material glow green when expressed. Embodiments using this feature allow verification of the viability of the cells, bacteria, or gene sequences in a matrix. The visibility of such a marker also assists in recovering an implanted electroprocessed composition.

Although the present invention provides versatility in release kinetics, embodiments also exist in which one or more substances are not released at all from the electroprocessed material. Substances may perform a function at a desired site. For example, in some embodiments, antibodies for a specific molecule are immobilized on an electroprocessed matrix and the composition is placed at a desired site. In this embodiment, the antibodies acts to bind the molecules in the vicinity of the composition. This embodiment is useful for isolating molecules that bind to an antibody. Another example is an electroprocessed matrix containing immobilized substrates that will bind irreversibly to an undesirable enzyme and thereby inactivate the enzyme.

The compositions of the present invention may be combined with pharmaceutically or cosmetically acceptable carriers and administered as compositions in vitro or in vivo. Forms of administration include but are not limited to injections, solutions, creams, gels, implants, pumps, ointments, emulsions, suspensions, microspheres, particles, microparticles, nanoparticles, liposomes, pastes, patches, tablets, transdermal delivery devices, sprays, aerosols, or other means familiar to one of ordinary skill in the art. Such pharmaceutically or cosmetically acceptable carriers are commonly known to one of ordinary skill in the art. Pharmaceutical formulations of the present invention can be prepared by procedures known in the art using well known and readily available ingredients. For example, the compounds can be formulated with common excipients, diluents, or carriers, and formed into tablets, capsules, suspensions, powders, and the like. Examples of excipients, diluents, and carriers that are suitable for such formulations include the following: fillers and extenders (e.g., starch, sugars, mannitol, and silicic derivatives); binding agents (e.g., carboxymethyl cellulose and other cellulose derivatives, alginates, gelatin, and polyvinyl-pyrrolidone); moisturizing agents (e.g., glycerol); disintegrating agents (e.g., calcium carbonate and sodium bicarbonate); agents for retarding dissolution (e.g., paraffin); resorption accelerators (e.g., quaternary ammonium compounds); surface active agents (e.g., cetyl alcohol, glycerol monostearate); adsorptive carriers (e.g., kaolin and bentonite); emulsifiers; preservatives; sweeteners; stabilizers; coloring agents; perfuming agents; flavoring agents; lubricants (e.g., talc, calcium and magnesium stearate); solid polyethyl glycols; and mixtures thereof.

The terms "pharmaceutically or cosmetically acceptable carrier" or "pharmaceutically or cosmetically acceptable vehicle" are used herein to mean, without limitations, any liquid, solid or semi-solid, including but not limited to water or saline, a gel, cream, salve, solvent, diluent, fluid ointment base, ointment, paste, implant, liposome, micelle, giant micelle, and the like, which is suitable for use in contact with living animal or human tissue without causing adverse physiological or cosmetic responses, and which does not interact with the other components of the composition in a deleterious manner. Other pharmaceutically or cosmetically acceptable carriers or vehicles known to one of skill in the art may be employed to make compositions for delivering the molecules of the present invention.

The formulations can be so constituted that they release the active ingredient only or preferably in a particular location, possibly over a period of time. Such combinations provide yet a further mechanism for controlling release kinetics. The coatings, envelopes, and protective matrices may be made, for example, from polymeric substances or waxes.

Methods of in vivo administration of the compositions of the present invention, or of formulations comprising such compositions and other materials such as carriers of the present invention that are particularly suitable for various forms include, but are not limited to, oral administration (e.g. buccal or sublingual administration), anal administration, rectal administration, administration as a suppository, topical application, aerosol application, inhalation, intraperitoneal administration, intravenous administration, transdermal administration, intradermal administration, subdermal administration, intramuscular administration, intrauterine administration, vaginal administration, administration into a body cavity, surgical administration at the location of a tumor or internal injury, administration into the lumen or parenchyma of an organ, and parenteral administration. Techniques useful in the various forms of administrations above include but are not limited to, topical application, ingestion, surgical administration, injections, sprays, transdermal delivery devices, osmotic pumps, electrodepositing directly on a desired site, or other means familiar to one of ordinary skill in the art. Sites of application can be external, such as on the epidermis, or internal, for example a gastric ulcer, a surgical field, or elsewhere.

The compositions of the present invention can be applied in the form of creams, gels, solutions, suspensions, liposomes, particles, or other means known to one of skill in the art of formulation and delivery of therapeutic and cosmetic compounds. Ultrafine particle sizes of electroprocessed materials can be used for inhalation delivery of therapeutics. Some examples of appropriate formulations for subcutaneous administration include but are not limited to implants, depot, needles, capsules, and osmotic pumps. Some examples of appropriate formulations for vaginal administration include but are not limited to creams and rings. Some examples of appropriate formulations for oral administration include but are not limited to: pills, liquids, syrups, and suspensions. Some examples of appropriate formulations for transdermal administration include but are not limited to gels, creams, pastes, patches, sprays, and gels. Some examples of appropriate delivery mechanisms for subcutaneous administration include but are not limited to implants, depots, needles, capsules, and osmotic pumps. Formulations suitable for parenteral administration include but are not limited to aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. Extemporaneous injection solutions and suspensions may be prepared from sterile powders, granules and tablets commonly used by one of ordinary skill in the art.

Embodiments in which the compositions of the invention are combined with, for example, one or more "pharmaceutically or cosmetically acceptable carriers" or excipients may conveniently be presented in unit dosage form and may be prepared by conventional pharmaceutical techniques. Such techniques include the step of bringing into association the compositions containing the active ingredient and the pharmaceutical carrier(s) or excipient(s). In general, the formulations are prepared by uniformly and intimately bringing into association the active ingredient with liquid carriers. Preferred unit dosage formulations are those containing a dose or unit, or an appropriate fraction thereof, of the administered ingredient. It should be understood that in addition to the ingredients particularly mentioned above, formulations comprising the compositions of the present invention may include other agents commonly used by one of ordinary skill in the art. The volume of administration will vary depending on the route of administration. For example, intramuscular injections may range in volume from about 0.1 ml to 1.0 ml.

The compositions of the present invention may be administered to persons or animals to provide substances in any dose range that will produce desired physiological or pharmacological results. Dosage will depend upon the substance or substances administered, the therapeutic endpoint desired, the desired effective concentration at the site of action or in a body fluid, and the type of administration. Information regarding appropriate doses of substances are known to persons of ordinary skill in the art and may be found in references such as L.S. Goodman and A. Gilman, eds, *The Pharmacological Basis of Therapeutics,* Macmillan Publishing, New York, and Katzung, *Basic & Clinical Pharmacology,* Appleton & Lang, Norwalk, Conn., (6$^{th}$ Ed. 1995). One desirable dosage range is 0.01 μg to 100 mg. Another desirable dosage range is 0.1 μg to 50 mg. Another desirable dosage range is 0.1 pg to 1.0 μg. A clinician skilled in the art of the desired therapy may chose specific dosages and dose ranges, and frequency of administration, as required by the circumstances and the substances to be administered. For example, a clinician skilled in the art of hormone replacement therapy may chose specific dosages and dose ranges, and frequency of administration, for a substance such as progesterone, to be administered in combination with the estrogenic and estrogenic modulatory molecules as required by the circumstances. For example, progesterone, and other progestins known to one of skill in the art may be administered in amounts ranging from about 50 μg to 300 mg, preferably 100 μg to 200 mg, more preferably 1 mg to 100 mg. Specific dosages and combinations of dosages of estrogenic and estrogenic modulatory molecules and progestins will depend on the route and frequency of administration, and also on the condition to be treated. For example, when the composition is formulated for oral administration, preferably in the form of a dosage unit such as a capsule, each dosage unit may preferably contain 1 μg to 5 mg of estrogenic and estrogenic modulatory molecules and 50 μg to 300 mg of progesterone. U.S. Pat. No. 4,900,734 provides additional examples of acceptable dose combinations of estrogenic molecules and progestins.

Other Uses Involving Electrically or Magnetically Active Constituents

The compositions of the present invention have a number of additional uses aside from substance delivery. Embodiments exist in which the incorporation of electrically or magnetically active constituents in the electroprocessed material allows the electroprocessed material to move rhythmically in response to an oscillating electric or magnetic field. Such an electroprocessed material can be used, for example, in a left ventricular assist device by providing a pumping action or a ventricular massage to a heart patent. Oscillations can be accomplished by passive movement of a magnetic or electric field with respect to the conductive material, or vice versa. By manipulating material selection, the electroprocessed material can be designed to remain in place permanently or to dissolve over time, eliminating the need for surgery to recover the device once the heart had recovered sufficiently.

Embodiments also exist in which an implanted electroprocessed material is used to convey an electric charge or current to tissue. For example, electrically active constituents can be electrically stimulated to promote neural ingrowth, stem cell differentiation, or contraction of engineered muscle, or to promote the formation of bone in orthopedic applications in which electroprocessed material is used as a carrier to reconstruct bone. In one embodiment, for example, an electroprocessed material is applied to a bone injury site and used to apply an electric current to the material to facilitate and to promote healing. The application of a small electric current to an injured bone is known to accelerate healing or promote the healing of bone injuries.

In other embodiments involving magnetically reactive materials, a magnetic field is used to position an electroprocessed material containing substances by relatively non-invasive means, for example by directing the movement of the material within the peritoneum. In other embodiments, a composition containing electrically active compounds is used to produce electric field-driven cell migration. This approach accelerates the healing process and minimize the risk of bacterial colonization. In one example, an orthopedic implant is coated with a very thin (<100 microns) layer of an electrically active polymer. With a very thin electrode attached to the coating, upon post-implantation, an electric field can be applied via an external electrode such that the electric field-driven cell migration is towards the implant surface. The direction can be reversed if so desired. Field orientation depends on the geometry of the implant and external electrode.

Use in Gene Therapy

Compositions of the present invention are also useful for testing and applying various gene therapies. By working with the compositions in vitro, different types of gene therapy and manipulation can be achieved by inserting preselected DNA in suspensions of cells, materials, etc. For example, nonviral techniques such as electroporation are used to treat cultured cells prior to insertion into the matrix of the present invention. In other embodiments, cells are treated within the matrix before the composition is inserted into a recipient. In vitro gene transfer avoids the exposure of a recipient to viral products, reduces risk of inflammation from residual viral particles and avoids the potential for germ cell line viral incorporation. It avoids the problem of finding or engineering viral coats large enough to accept large genes such as the one for Factor VIII (anti-hemophilic factor). However, in vivo gene therapy is accomplished in some embodiments by, for example, incorporating DNA into the electroprocessed material as it is created through the electroprocessing techniques of the present invention, whereby some DNA will be incorporated into the in vivo cells in contact with the composition after application of the composition to the recipient. This is especially true of small gene sequences, such as antisense oligonucleotides.

Use of an Electroprocessed Composition as Tissue or Organ Replacement

The ability to combine cells in an electroprocessed material provides the ability to use the compositions of the present invention to build tissue, organs, or organ-like tissue. Cells included in such tissues or organs can include cells that serve a function of delivering a substance, seeded cells that will provide the beginnings of replacement tissue, or both. Many types of cells can be used to create tissue or organs. Stem cells, committed stem cells, and/or differentiated cells are used in various embodiments. Also, depending on the type of tissue or organ being made, specific types of committed stem cells are used. For instance, myoblast cells are used to build various muscle structures, neuroblasts are employed to build nerves, and osteoblasts are chosen to buildbone. Examples of stem cells used in these embodiments include but are not limited to embryonic stem cells, bone marrow stem cells and umbilical cord stem cells used to make organs or organ-like tissue such as livers, kidneys, etc. Examples of tissue embodiments that use differentiated cells include fibroblasts in a matrix used for a patch, for example a hernia patch, endothelial cells for skin, osteoblasts for bone, and differentiated cells like cadaver donor pancreatic islet cells for a delivery device to place these cells in a specific site, for example the liver. In some embodiments the shape of the electroprocessed composition helps send signals to the cells to grow and reproduce in a specific type of desired way. Other substances (for example, differentiation inducers) can be added to the electroprocessed matrix to promote specific types of cell growth. Further, different mixtures of cell types are incorporated into the composition in some embodiments.

In certain disease states, organs are scarred to the point of being dysfunctional. A classic example is cirrhosis. In cirrhosis, normal hepatocytes are trapped in fibrous bands of scar tissue. In one embodiment of the invention, the liver is biopsied, viable liver cells are obtained then cultured in an electroprocessed matrix, and reimplanted in the patient as a bridge to or replacement for routine liver transplantations.

Mixing of committed cell lines in a three dimensional electroprocessed matrix can be used to produce structures that mimic complex organs. For example, by growing glucagon secreting cells, insulin secreting cells, somatostatin secreting cells, and/or pancreatic polypeptide secreting cells, or combinations thereof, in separate cultures, and then mixing them together with electroprocessed materials through electroprocessing, an artificial pancreatic islet is created. These structures are then placed under the skin, retroperitoneally, intrahepatically or in other desirable locations, as implantable, long-term treatments for diabetes.

In other examples, hormone-producing cells are used, for example, to replace anterior pituitary cells to affect synthesis and secretion of growth hormone secretion, luteinizing hormone, follicle stimulating hormone, prolactin and thyroid stimulating hormone, among others. Gonadal cells, such as Leydig cells and follicular cells are employed to supplement testosterone or estrogen levels. Specially designed combinations are useful in hormone replacement therapy in post and perimenopausal women, or in men following decline in endogenous testosterone secretion. Dopamine-producing neurons are used and implanted in a matrix to supplement defective or damaged dopamine cells in the substantia nigra. In some embodiments, stem cells from the recipient or a donor can be mixed with slightly damaged cells, for example pancreatic islet cells, or hepatocytes, and placed in an electroprocessed matrix and later harvested to control the differentiation of the stem cells into a desired cell type. This procedure is performed in vitro or in vivo. The newly formed differentiated cells are introduced into the patient.

The ability to use electroprocessed materials and matrices to bioengineer tissue or organs creates a wide variety of bioengineered tissue replacement applications. Examples of bioengineered components include, but are not limited to, skeletal muscle, cardiac muscle, nerve guides, brain constructs as a filler for damaged/removed areas of the brain that are lost during accident or disease, a filler for other missing tissues, cartilage scaffoldings, sheets for cosmetic repairs, skin (sheets with cells added to make a skin equivalent), vascular grafts and components thereof, and sheets for topical applications (skin covering but no additional cells, just a patch). In some embodiments, such matrices are combined with drug and substance delivery electroprocessed matrices of the present invention in ways that will improve the function of the implant. For example, antibiotics, anti-inflammatories, local anesthetics or combinations thereof, can be added to the matrix of a bioengineered organ to speed the healing process and reduce discomfort.

One method or preparing implants of the present invention is use of a bioreactor. There are several kinds of commercially available bioreactors, devices designed to provide a low-shear, high nutrient perfusion environment. Until recently, most of the available bioreactors maintained cells in suspension and delivered nutrients and oxygen by sparging, through the use of impellers, or other means of stirring. The RCCS bioreactor (Synthecon) is a rotating wall bioreactor. It consists of a small inner cylinder, the substrate for the electrospinning process, positioned inside a larger outer cylinder. Although the electrospun or electroaerosol matrix can be fabricated on the inner cylinder, other locations within the bioreactor also can be used for placement of a matrix for seeding. The gap between the inner and outer cylinders serves as the culture vessel space for cells. Culture medium is oxygenated via an external hydrophobic membrane. The low shear environment of the Synthecon RCCS bioreactor promotes cell-cell and cell-extracellular matrix (ECM) interactions without the damage or "washing away" of nutrients that occurs with active stirring or sparging. Typically, the RCCS device is operated at rotation rates of 8 up to 60 RPM, as required to maintain cells in suspension, and at less than 8 RPM (preferably 2-3 RPM) for cultures immobilized along the center shaft of the vessel. The Synthecon bioreactor can be used in a standard tissue culture incubator. These values for spin rates and other parameters can be varied depending on the specific tissue created.

Electroprocessed materials, such as matrices, are useful in formation of prostheses. One application of the electroprocessed matrices is in the formation of medium and small diameter vascular prostheses. Some preferred materials for this embodiment are collagen and elastin, especially collagen type I and collagen type III. Some examples include, but are not limited to coronary vessels for bypass or graft, femoral artery, popliteal artery, brachial artery, tibial artery, radial artery or corresponding veins. The electroprocessed material is useful especially when combined with endothelial cells on the inside of the vascular prosthesis, and smooth muscle cells, for example a collagen tube, and also when combined with fibroblasts on the outside of the collagen tube. More complicated shapes including tapered and/or branched vessels can also be constructed. A different-shaped mandrel is necessary to wind the large fibers around or to orient the electrospun/electroaerosol polymer.

Combination of electroprocessed matrix materials and wound polymer fibers can provide optimal growth conditions for cells. The polymer forms a basic structural matrix and the electroprocessed matrix is used to deliver the cells. This facilitates cell attachment onto the structural matrix. Furthermore the stress in the polymer also orients fibers in the matrix providing further spatial cues for the cells.

In an alternative fabrication strategy, a cylindrical construct is electrospun onto a suitable target, for example a cylindrical mandrel. Other shapes can be used if desirable based upon the shape of the site into which the implant will be placed. Matrices in this embodiment are composed, for example, of electroprocessed fibrinogen/fibrin (for example to promote neovascularization, cellular integration and infiltration from the surrounding tissue), electroprocessed collagen (to promote cell infiltration and lend mechanical integrity), and other components, for example PGA, PLA, and PGA-PLA blends, PEO, PVA or other blends. The relative ratio of the different components of this construct is tailored to specific applications (e.g. more fibrin, less collagen for enhanced vascularization in a skin graft). To fabricate a cylindrical muscle the construct is filled with muscle or stem cells or other cell type and the distal ends of the electrospun constructs are sutured or sealed shut. In some embodiments, cells are mixed with various matrix materials to enhance their distribution within the construct. For example, the cells can be mixed with electroprocessed fibrin or collagen prior to insertion into the construct. The objective of this strategy is to provide additional mechanical support to the construct and provide the cells with a three dimensional matrix within the construct to promote growth. This also helps to maintain the cells in an even distribution within the construct. This method can be used to enhance the alignment of the cells within the construct. This filling material can be extruded directly into the cylindrical construct, as the filling is extruded, alignment occurs. Mixing endothelial cells with the other cells inserted into the construct (or other cell types) can be done to accelerate neovascularization. Another method to accomplish this objective is to electrodeposit endothelial cells directly into the electroprocessed collagen-matrix that aids in formation of the cylindrical sheath. The alignment of the fibers within the electroprocessed matrix that comprises the construct are optionally controlled by controlling the relative movement of the target and source, solution with respect to one another. Other cell types, such as tendon fibroblasts, are optionally electrospun into or onto the outer surface of the construct to enhance the formation of the outer connective tissue sheath that forms the construct.

In another example a sheet of electroprocessed material is prepared, rolled into a cylinder and inserted into an electroprocessed cylinder. The construct is filled with cells as described above, sutured shut and placed in a bioreactor or directly in situ. By aligning the fibrils of the electrospun sheet of material in parallel with the long axis of the outer cylinder a muscle-like, electroprocessed composition is produced. Cells in contact with the fibrils that are arrayed along the long axis of the sheet spread in parallel with the fibrils of the sheet, forming a muscle construct of cells arrayed and layered in a pattern of organization similar to that present in vivo. The cylindrical tissue construct is then implanted or placed within a RCCS bioreactor. Rates of rotation to maintain this type of construct in suspension range from 4-20 rpm, depending upon the over mass of the tissue and the specific materials used to fabricate the outer cylinder.

Vascularization of the engineered tissue containing electroprocessed matrix material will occur in situ several days after surgery. In some embodiments, neovascularization of an engineered construct containing electroprocessed material is enhanced by mixing endothelial cells into the construct during fabrication. Another alternative for supplying engineered tissue containing electroprocessed material with a vascular supply is to temporarily transplant the tissue into the omentum. The omentum has an extensive and rich vascular supply that can be used like a living incubator for the support of engineered tissue. The engineered tissue is removed from a bioreactor, wrapped in the omentum and supported by the diffusion of nutrients and oxygen from the surrounding tissue in the omentum. Alternatively, or in addition to this approach, engineered tissue is connected directly to the endogenous vascular supply of the omentum. A blood vessel can be partially perforated or cut or left dissected free of the omentum. The engineered tissue containing electroprocessed collagen, fibrin, or other materials, depending upon the construct, is wrapped around the vessel. The engineered tissue is supported by nutrients leaking from the perforated vessel or by the simple diffusion of nutrients if the vessel is left intact. Regardless of strategy, the engineered tissue is surrounded by the omentum and its rich vascular supply.

Tissue containing electroprocessed material can be engineered with an endogenous vascular system. This vascular system can be composed of artificial vessels or blood vessels excised from a donor site on the transplant recipient. The engineered tissue containing electroprocessed matrix material is then assembled around the vessel. By enveloping such a vessel with the tissue during or after assembly of the engineered tissue, the engineered tissue has a vessel that can be attached to the vascular system of the recipient. In this example, a vessel in the omentum, or other tissue is cut, and the vessel of the engineered tissue is connected to the two free ends of the omental vessel. Blood passes from the omental vessel into the vascular system of the engineered tissue, through the tissue and drains back into the omentum vessel. By wrapping the tissue in the omentum and connecting it to an omental blood vessel, the engineered tissue is supported by the diffusion of nutrients from the omentum and the vessel incorporated into the tissue during its fabrication. After a suitable period of time the tissue is removed from the omentum and placed in the correct site in the recipient. By using this strategy the engineered tissue containing electroprocessed material is supported in a nutrient rich environment during the first several days following removal from the bioreactor. The environment of the omentum also promotes the formation of new blood vessels in implanted tissue. This omental incubator strategy can be combined with the other strategies such as combining angiogenic factors in the matrix material during electroprocessing. Several options are available. First, the implants can be seeded with angioblasts and/or endothelial cells to accelerate the formation of vascular elements once the engineered tissue is placed in situ. Second, angiogenic peptides can be introduced into the engineered tissue via an osmotic pump. The use of an osmotic pump permits delivery of peptides or, as noted, angiogenic peptides or growth factors directly to the site of interest in a biologically efficient and cost-effective manner. VEGF delivered to ischemic hind limbs of rabbits accelerated capillary bed growth, increased vascular branching and improved muscular performance with respect to ischemic controls. An alternative approach is to seed fully differentiated tissue constructs containing electroprocessed matrix material with additional endothelial cells and or angioblasts shortly before they are implanted in situ.

In some embodiments, the stem cells or other cells used to construct the implant are isolated from the subject, or other compatible donor requiring tissue reconstruction. This provides the advantage of using cells that will not induce an immune response, because they originated with the subject (autologous tissue) requiring the reconstruction. Relatively small biopsies can be used to obtain a sufficient number of cells to construct the implant. This minimizes functional deficits and damage to endogenous tissues that serve as the donor site for the cells.

In some embodiments, the matrices of the present invention include substances in the matrix that will improve the performance of the implanted electroprocessed matrix. Examples of substances that can be used include peptide growth factors, antibiotics, and/or anti-rejection drugs. Alternatively, cells that are engineered to manufacture desired compounds can be included. The entire construct is, for example, cultured in a bioreactor or conventional culture or placed directly in vivo. For example, neovascularization can be stimulated by angiogenic and growth-promoting factors, administered, as peptides, proteins or as gene therapy. Angiogenic agents can be incorporated into the electroprocessed matrix. Nerve growth factors can be electrospun into the matrix to promote growth or neurons into the matrix and tissue. In a degradable matrix, the gradual degradation/breakdown of the matrix will release these factors and accelerate growth of desired tissues.

Electroprocessed matrices can also be used in connection with other matrix building processes. In other words, an extruded tube can have an outside layer electrospun onto it wherein the different layers complement each other and provide an appropriate matrix to promote a specific type of cell growth. As an example, a vascular graft comprised primarily of a collagen tube can have an electrospun layer of both other materials such as collagen or fibrin and cells added to promote the acceptability of the graft in a particular recipient. A second example is an in vitro skin preparation formed by growing fibroblasts in one layer, covering the first layer with electroprocessed collagen, and then growing a second layer composed of epidermal cells in the fibrin matrix. This layering technique can be used to make a variety of tissues.

Stability and Storage of the Electroprocessed Compositions

The stability of the compositions of the present invention comprising electroprocessed materials combined with substances also allows for long term storage of the compositions between formation and use. Stability allows greater flexibility for the user in embodiments in which a drug or other substance is applied after formation of the electroprocessed material, for example by soaking and spraying. A formed electroprocessed matrix can be fabricated and stored, and then the exact substance composition to be delivered to an individual patient can be prepared and tailored to a specific need shortly before implantation or application. This feature allows users greater flexibility in both treatment options and inventory management. Many electroprocessed materials are dry once they are spun, essentially dehydrated, thereby facilitating storage in a dry or frozen state. Further, the electroprocessed compositions are substantially sterile upon completion, thereby providing an additional advantage in therapeutic and cosmetic applications.

Storage conditions for the compositions of the present invention will depend on the electroprocessed materials and substances therein. In embodiments involving proteins, for example, it may be necessary or desirable to store the compositions at temperatures below 0° C., under vacuum, or in a lyophilized condition. Other storage conditions can be used, for example, at room temperature, in darkness, in vacuum or under reduced pressure, under inert atmospheres, at refrigerator temperature, in aqueous or other liquid solutions, or in powdered form. Persons of ordinary skill in the art recognize appropriate storage conditions for the materials and substances contained in the compositions and will be able to select appropriate storage conditions.

The compositions of the present invention and formulations comprising those compositions may be sterilized through conventional means known to one of ordinary skill in the art. Such means include but are not limited to filtration, radiation, and heat. The compositions the present invention may also be combined with bacteriostatic agents, such as thimerosal, to inhibit bacterial growth.

Formulations comprising the compositions of the present invention may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art. Preferred unit dosage formulations are those containing a dose or unit, or an appropriate fraction thereof, of the administered ingredient. It should be understood that in addition to the ingredients particularly mentioned above, the formulations of the present invention may include other agents commonly used by one of ordinary skill in the art.

The compositions of the present invention may be packaged in a variety of ways depending upon the method used for administering the composition. Generally, an article for distribution includes a container which contains the composition or a formulation comprising the composition in an appropriate form. Suitable containers are well-known to those skilled in the art and include materials such as bottles (plastic and glass), sachets, ampules, plastic bags, metal cylinders, and the like. The container may also include a tamper-proof assemblage to prevent indiscreet access to the contents of the package. In addition, the container has deposited thereon a label which describes the contents of the container. The label may also include appropriate warnings.

The present invention is further illustrated by the following examples, which are not to be construed in any way as imposing limitations upon the scope thereof. On the contrary, it is to be clearly understood that resort can be had to various other embodiments, modifications, and equivalents thereof, which, after reading the description herein, can suggest themselves to those skilled in the art without departing from the spirit of the present invention.

EXAMPLE 1

Fibroblast growth factor (FGF, obtained from Chemicon, Temecula, Calif.) was dissolved in a solution of matrix material comprised of type I collagen (80%), PGA (10%) and PLA (10%). The percentages refer to the weight of the materials with respect to one another. These materials were dissolved in HFIP at a final concentration of 0.08 gm per ml. Sufficient FGF was added to 1 ml of solution to provide an FGF concentration of 50 ng/ml of the collagen/PGA/PLA electrospinning solution. The material was electrospun into the shape of a cylinder onto the outer surface of a grounded and spinning 16 gauge needle about 25-35 mm in length. After application, the cylinder was sutured shut looping a suture around the outside of the construct and pulling tight to seal the ends. Alternatively, a hot forceps is used to pinch the ends together and literally heat seal the ends shut. These methods formed a hollow, enclosed construct. The construct was then surgically implanted within the vastus lateralis muscle of a rat. The construct was left in place for seven days and recovered for inspection. FGF in the matrix accelerated muscle formation within the electrospun matrix by promoting muscle formation within the wall of the electrospun cylinder.

EXAMPLE 2

Vascular endothelial growth factor (VEGF, obtained from Chemicon, Temecula, Calif.) was dissolved in a solution of matrix material comprised of type I collagen (80%), PGA (10%) and PLA (10%) as described in EXAMPLE 1. These materials were dissolved in HFIP at a final concentration of 0.08 gm per ml. Sufficient VEGF was added to 1 ml of solution to provide a VEGF concentration of 50 ng/ml of the collagen/PGA/PLA electrospinning solution. The material was electrospun to form a construct and implanted into a rat muscle using the same procedures set forth in Example 1. VEGF increased the density of functional capillaries that were present throughout the construct. This was evidenced by the presence of capillaries containing red blood cells (RBCs).

EXAMPLE 3

Constructs of electroprocessed collagen and PGA:PLA copolymer, with VEGF spun into the matrix were prepared using 80% collagen and 20% PGA:PLA. The collagen and PGA:PLA were dissolved in HFIP at a final combined concentration of 0.08 gm per ml. Solutions were prepared in which different amounts of VEGF were added to 1 ml of the solution of collagen and PGA:PLA copolymer. Separate solutions were prepared containing 0 ng, 25 ng, 50 ng, and 100 ng each in 1 ml. Constructs were prepared for each solution by electrospinning one ml. The constructs were cut into smaller sections and placed in a phosphate buffer solution (PBS). Release of VEGF into the PBS was measured as a function of time by the ELISA method. The ELISA kit for VEGF was purchased from Chemicon International (part number cyt214) and the directions provided in the kit were followed to perform the ELISA. Samples were centrifuged to remove particulate matter and stored at −20° C. prior to use.

An identical construct was subjected to crosslinking by exposing it to glutaraldehyde vapor at room temperature and subjected to an identical ELISA assay. A sample of the electroprocessed construct was placed in a 100 mm tissue culture dish. A 35 mm tissue culture dish containing 1 ml of 50% glutaraldehyde was placed inside the 100 mm tissue culture dish. The lid of the 100 mm tissue culture dish was replaced and the sample was allowed to sit for 15 minutes at room temperature. The sample was rinsed in sterile water or culture media. The amount of VEGF (expressed in picograms per 1 mg of electrospun material) for the non cross-linked and cross-linked samples was measured at different times are presented in FIGS. 3 and 4, respectively.

Figure 3:
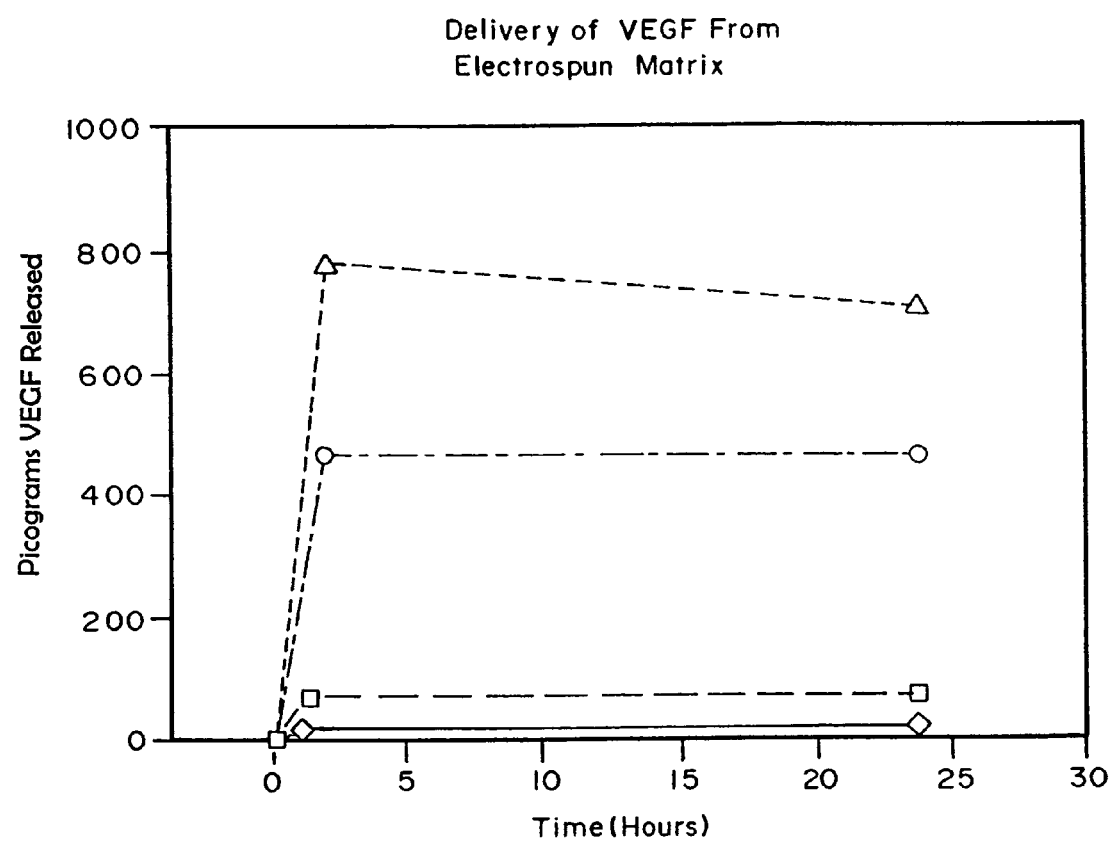
FIG. 3 is a graph showing the release profile of vascular endothelial growth factor (VEGF) from one embodiment of the present invention obtained by electrospinning a solution comprising collagen, polylactic acid (PLA), polyglycolic acid (PGA), and VEGF.
Figure 4:
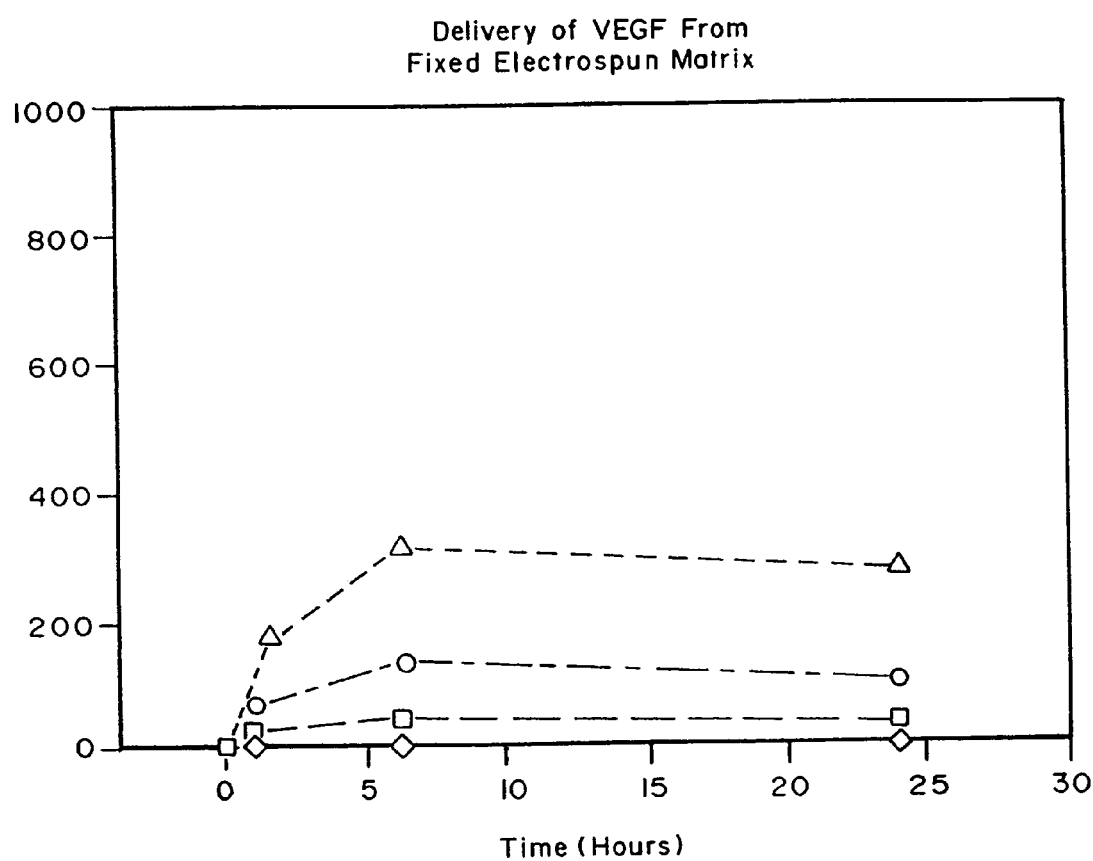
FIG. 4 is a graph showing the release profile of VEGF from an embodiment of the present invention obtained by electrospinning a solution comprising collagen, polylactic acid, and polyglycolic acid, and VEGF and subsequently cross-linking the electroprocessed material by exposure to glutaraldehyde vapor.

In FIG. 3 and FIG. 4, the open diamonds represent release from the fibers electrospun from the solution containing PGA:PLA copolymer and collagen to which no VEGF was added. The open squares represent release from fibers electrospun from the solution containing PGA:PLA copolymer and collagen to which 25 ng of VEGF were added. The open circles represent release from the fibers electrospun from a solution containing PGA:PLA copolymer and collagen to which 50 ng of VEGF were added. The open triangles represent release from the fibers electrospun from a solution containing PGA:PLA copolymer and collagen to which 100 ng of VEGF were added. Results demonstrate not only that the matrix releases VEGF in PBS but also that crosslinking with glutaraldehyde slows release from the matrix.

EXAMPLE 4

Polyethylene-co-vinyl acetate) (PEVA) was a gift from DuPont (Elvax 40, 40 vinyl acetate). PEVA pellets were soaked in ethanol for several days to remove antioxidants. Poly(lactic acid) (100 L PLA) was a gift from by Alkermes, Inc. (Medisorb®)) with a number-average molecular weight, $M_n$, of 205 KD and polydispersity of 1.7. All solvents were analytical grade and were used as received. Tris(hydroxymethyl)aminomethane hydrochloride (Trizma® HCl) and trishydroxymethylaminomethane (Trizma®-base) were supplied by Sigma and were used without further purification to prepare buffer solutions of pH 7.35. Tetracycline hydrochloride was also obtained from Sigma. Actisite® periodontal fiber (0.5 rrim PEVA) containing 25 wt % tetracycline hydrochloride was a gift from Alza Corporation (Palo Alto, Calif.).

Electrospinning was carried out using 14% wt/v solutions of 100% PEVA, 100% PLA, or mixtures of the two in chloroform. The mixtures used were 25% PEVA/75% PLA, 50%/50% of each, and 75% PEVA/25% PLA, with percentages by weight. Tetracycline hydrochloride, which is insoluble in chloroform, was solubilized in a small amount of methanol and added to the polymer solutions prior to electrospinning. The resulting solutions were yellow but clear, indicating homogeneous solubilization of both the polymers and drug.

The electrospinning set-up consisted of a glass pipette (held parallel to ground or angled at 45° downward), 0.32 mm diameter silver-coated copper wire (positive lead), a copper sheet (ground electrode) ca. 30 cm from the pipette, and a Spellman CZE100OR high voltage supply. A positive voltage (15 kV) was applied through the copper wire to the polymer solution inside the glass pipette. The solutions were delivered via syringe pumps to control the mass flow rate, which ranged from 10-18 ml/h. More conveniently, the solution can be held in a plastic syringe with the high voltage supply connected to the metal syringe needle. The solutions were delivered via syringe pumps to control the mass flow rate, which ranged from 10-18 ml/h. The resulting electrically charged fibers were collected on a rotating metal plate to produce a sheet of non-woven fabric.

A 100L PLA containing 5% tetracycline hydrochloride (by weight) was electrospun from 14% W/V solution in chloroform, with a mass flow rate of the polymer solution between 18-21 ml/h. PEVA containing 5% tetracycline hydrochloride (expressed herein as by weight of total polymer) was electrospun from 14% W/V solution with a mass flow rate of 3 ml/h. Blends containing 5% tetracycline hydrochloride and consisting of 25% PLA and 75% PEVA were electrospun at mass flow rates of 13-18 ml/h. A 50/50 PLA/PEVA blend with 5% tetracycline hydroxide was spun at a mass flow rate of 10-13 ml/h. A 50/50 PLA/PEVA blend with 25% tetracycline hydroxide (by weight of total polymer weight) was spun at a mass flow rate of 15 ml/hr. A blend containing 75/25 PLA/PEVA with 5% tetracycline hydroxide was spun with a mass flow rate of 17 ml/h. The collected 'fabric' was used for studying the release of tetracycline hydrochloride.

For comparative purposes, cast films were made from different compositions of PLA and PEVA. As with the fibers, films were made of 25% PEVA/75% PLA, 50%/50% of each, and 75% PEVA/25% PLA and 5% tetracycline hydrochloride was added to each. The solutions in chloroform were cast onto glass petri dishes, left at room temperature until the chloroform was evaporated, then dried at 25° C. under vacuum for 3 hours. The release of tetracycline hydrochloride from ACTISITE® (PEVA) periodontal fiber was also compared.

Release of tetracycline hydrochloride was determined using UV-VIS measurements carried out at Perkin-Elmer UV/VIS Lambda 40 Spectrophotometer. The molar extinction coefficient for tetracycline hydrochloride in Tris buffer was found to be 15,800 from a linear Beer-Lambert plot of absorbance at 360 nm vs. concentration. Release of tetracycline hydrochloride was determined by placing a known mass of polymer and drug in tris buffer and monitoring the absorbance at 360 nm as a function of time. The buffer solution was changed if the released drug gave absorbance higher than 2.0. Data are reported as the % tetracycline hydrochloride released based upon the expected amount in the samples from the feed composition. The morphology of the electrospun samples were studied with JSM-820 Scanning electron microscope (JEOL Ltd.).

Figure 5:
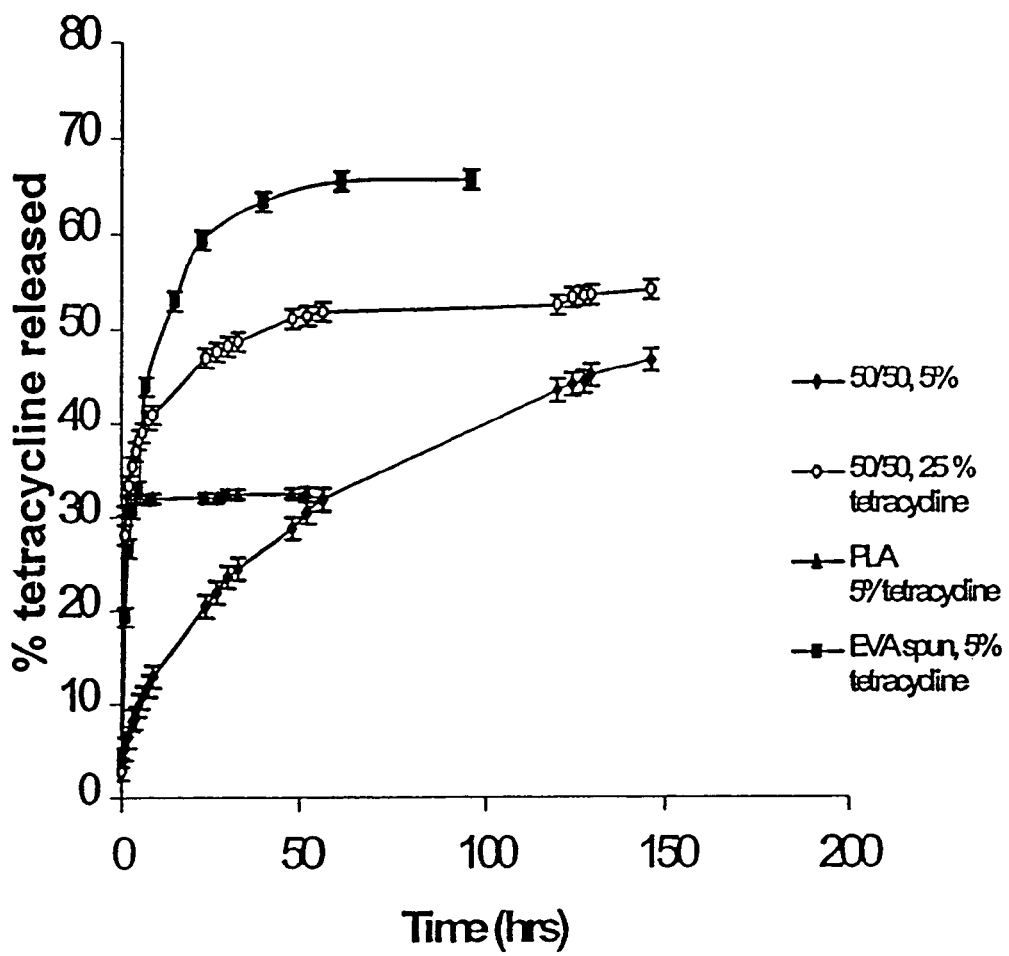
FIG. 5 is a graph showing the release profile of tetracycline from several embodiments of the present invention obtained by electrospinning solutions containing tetracycline along with PLA, poly(ethylene-co-vinyl acetate) or a combination of PLA and poly(ethylene-co-vinyl acetate).
Figure 6:
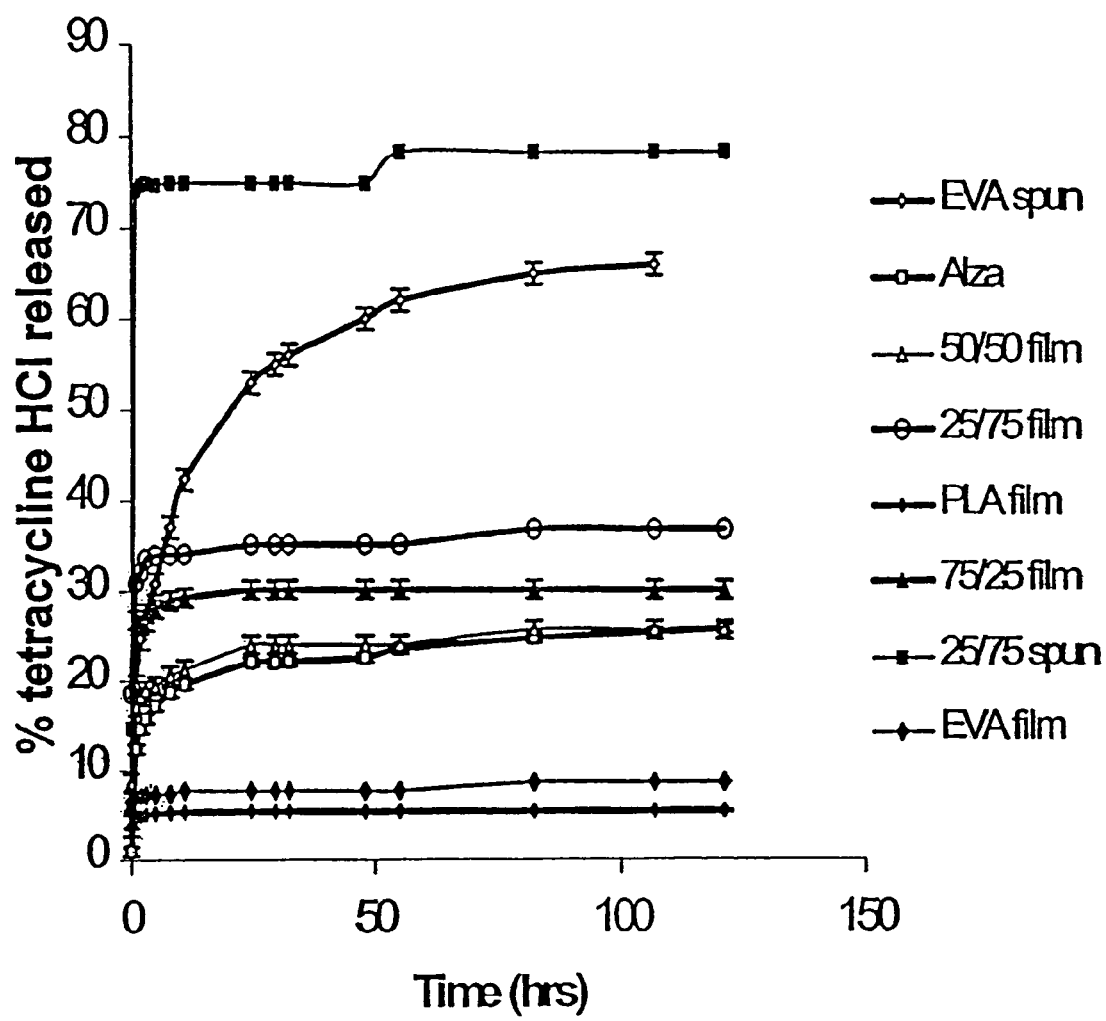
FIG. 6 is a graph comparing the release profile of tetracycline from an embodiment of the present invention and several other compositions. The embodiment of the present invention was obtained by electrospinning a solution containing tetracycline with poly(ethylene-co-vinyl acetate). The other compositions were periodontal fibers containing 25 wt % tetracycline hydrochloride and films containing tetracycline with polylactic acid, poly(ethylene-co-vinyl acetate) or a combination of polylactic acid and poly(ethylene-co-vinyl acetate).

The release profiles of tetracycline hydrochloride from electrospun fibers and the cast films are shown in FIGS. 5 and 6. In FIG. 5, the solid diamonds denote release from the fibers electrospun from the solution in which the polymer was 50% EVA and 50% PLA and 5% tetracycline was added. The open circles denote release from the fibers electrospun from the solution in which the polymer was 50% EVA and 50% PLA and 25% tetracycline was added. The open triangles denote release from the fibers electrospun from the solution in which the polymer was 100% PLA and 5% tetracycline was added. The solid squares denote release from the fibers electrospun from the solution in which the polymer was 100% EVA and 5% tetracycline was added.

In FIG. 6, the open diamonds denote release from the fibers electrospun from the solution containing 100% EVA. The open squares denote release from the ACTISITE® (PEVA) periodontal fiber. The open triangles denote release from the film in which the polymer was 50% PLA and 50% PEVA. The open circles denote release from the film in which the polymer was 25% PLA and 75% PEVA. The solid diamonds connected by a thick line denote release from the film containing 100% PLA. The solid triangles denote release from the film in which the polymer was 75% PLA and 25% PEVA. The solid squares denote release from the fibers electrospun from the solution containing 25% PLA and 75% PEVA. The solid diamonds connected by a thin line denote release from film containing 100% EVA.

Electrospun EVA showed a higher release rate than the mats derived from PLA/EVA (50/50) or pure PLA. Electrospun PEVA released 65% of its drug content within 100 hours, whereas the electrospun 50/50 mixture of PEVA and PLA released about 40% over the same time period. Mats of PLA fibers with no PEVA exhibit some instantaneous release, with negligible release over 50 hours. The 50:50 sample with 25 wt % tetracycline hydrochloride releases the drug more rapidly than the 5% sample, although the % released of the former approaches that of the latter after 150 hrs.

Figure 7:
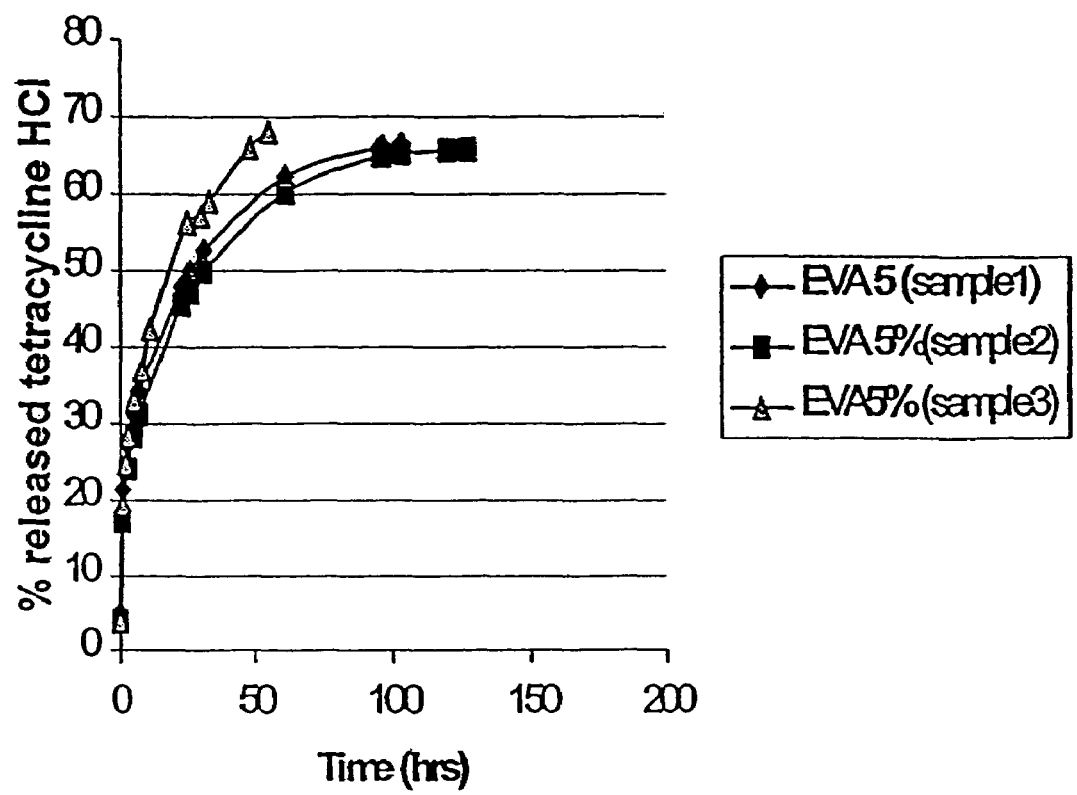
FIG. 7 is a graph showing the release profile of tetracycline from several embodiments of the present invention obtained by electrospinning solutions containing tetracycline with poly(ethylene-co-vinyl acetate).

FIG. 7 shows release profiles of three electrospun PEVA samples, two from the same batch of mat and another from a different preparation under identical conditions. The release amounts of each sample are denoted by solid diamonds, solid squares, and open triangles, respectively. The profiles are quite similar indicating very good reproducibility. In general, the initial rate of release of all formulations including ACTISITE® (denoted as Alza) is high during the first 10-12 hours, most likely due to release of drug sequestered on the sample surfaces. The total percent released from the cast films (FIG. 6) were lower than that of the electrospun mats, as would be expected due to the much lower surface area of the former. The PLA/EVA 75/25 film released 30% of its tetracycline hydrochloride in 120 hrs, whereas the film of 50/50 PLA/EVA showed a slightly lower percent of release (25%) in the same period of time. Release from the PLA film was much lower, only 6% released in 120 hrs, whereas the PEVA film showed 8% release over the same period.

EXAMPLE 5

A mixture of cultured insulin secreting cells is seeded into an electroprocessed collagen matrix to form an electroprocessed collagen-containing tissue. The electroprocessed matrix containing the insulin secreting cells is implanted into a diabetic recipient in need of insulin. This electroprocessed collagen or fibrin-containing tissue optionally contains a vessel. The matrix is implanted into the retroperitoneal space and the vessel is anastomosed into the hepatic portal circulation. Insulin is released from the insulin-containing cell and transmitted to the circulation.

The electroprocessed matrix containing the insulin secreting cells is optionally supplemented with cells that synthesize and secrete glucagon, somatostatin, pancreatic polypeptide, or combinations thereof, in order to mimic the hormonal complement of the pancreatic islet.

Optionally, heterologous cells, (for example, engineered bacteria or cells from a conspecific donor) are placed in a matrix with a pore size that will allows diffusion of nutrients to the cells but does not allow or inhibits or delays the detection of the cells by the recipient's immune system.

EXAMPLE 6

Keratinocytes are harvested from a healthy site of a patient suffering from a chronic wound. The cells are grown in culture and transfected by electroporation to express VEGF. Next, the transfected cells are mixed or prepared in an electrospun collagen matrix. Antisense oligonucleotide for matrix metalloproteinases (MMPs) are also spun into the matrix. The matrix is topically applied to the surface of the wound. The cells near and in the implant take up the antisense sequences, express their transfected gene sequences and MMP production is reduced. In other applications the cells may be genetically engineered to secrete VEGF, thereby promoting healing. Release of the antisense oligonucleotides suppress expression of MMPs, which are typically overexpressed in a chronic wound. Thus the wound site is repaired with an implant that simultaneously promotes natural healing responses. Optionally, the matrix is comprised of fibrin or a mix of fibrin and collagen. The fibrin assists in cessation of bleeding and promotes healing.

EXAMPLE 7

Osteoblasts from a patient with a bone injury are cultured and incorporated into an electrospun matrix comprising type I collagen. The matrix is formed in the shape of a cavity or defect at the injury site. Bone growth factor (BGF), bone morphogenic protein (BMP) or sequences of genes encoding for these proteins, are electrospun into the matrix are optionally incorporated into the electrospun matrix. The matrix assists in growth of new bone, and the BGF or BMP in the matrix promotes bone growth.

Optionally, the collagen used is produced in vitro by genetically engineered cells that express a collagen polymer with more P-15 sites than in normal collagen. The excess of P-15 sites promotes osteoblasts to produce and secretes hydroxyapatite and further aid bone growth.

Optionally, the matrix is further electroprocessed with polypyrroles, which are electrically active materials. Electrodes are attached to each end of the implanted matrix. Charged electrodes are later applied to the surface over the electrodes to create a small electric current across the implant to further facilitate healing of the bone injury. In another embodiment piezoelectric elements may be electrospun into the matrix to produce electric discharges that promote healing.

EXAMPLE 8

In another example, similar to that described for skeletal muscle a cardiac patch is prepared. A sheet of electroprocessed material is prepared with aligned filaments of collagen. The sheet is folded into a pleated sheet in the desired shape and or rolled into a cylinder. A second construct is electrospun in the desired shape, for example a rectangle. The pleated sheet that mimics the cellular layers of the intact heart is inserted into the electroprocessed rectangular form. The construct is filled with cells, sutured shut and placed in a bioreactor or directly in situ. By aligning the fibrils of the pleated electrospun sheet of material in parallel with the long axis of the outer rectangular form, a cardiac, muscle-like construct is obtained. Native cardiac tissue is composed of layers of cells arrayed along a common axis with adjacent cell layers slightly off axis with the overlaying and underlying layers. This structure is more precisely mimicked by the methods described below in which a matrix is prepared and cells are directly electroprocessed, dribbled or sprayed onto the matrix as it is prepared. Cells in contact with the fibrils that are arrayed along the long axis of the sheet spread in parallel with the underlying fibrils of the sheet, forming a muscle construct of cells arrayed and layered in an in vivo-like pattern of organization. The construct can be directly implanted or placed within a RCCS bioreactor. Rates of rotation to maintain this type of construct in suspension range from 4-20 rpm, depending upon the mass of the tissue and the specific materials used to fabricate the outer cylinder. Variations of this design include the addition of angiogenic factors in the matrix, gene sequences, and agents to suppress inflammation and/or rejection. Other cell types may be added to the construct, for example microvascular endothelial cells, to accelerate the formation of a capillary system within the construct. Other variations in this design principle can be used. For example, cells may be electroprocessed into the matrix as it is deposited on the ground target. By varying the pitch of the fibers during spinning and spraying, dribbling or electroprocessing cells onto the fibers as they are deposited very precisely controls the positioning of the cells within the construct.

All patents, publications and abstracts cited above are incorporated herein by reference in their entirety. It should be understood that the foregoing relates only to preferred embodiments of the present invention and that numerous modifications or alterations can be made therein without departing from the spirit and the scope of the present invention as defined in the following claims.

What is claimed is:

1. A composition comprising:
    an electroprocessed material and a substance, wherein the electroprocessed material is made by a method comprising the step of simultaneously electroprocessing a natural polymer that is an extracellular matrix protein or polymerized thrombin and two or more synthetic polymers, wherein the synthetic polymers are selected from the group consisting of poly(urethanes), poly (siloxanes), silicones, poly(ethylene), poly(vinyl pyrrolidone), poly(2-hydroxyethyl methacrylate), poly(N-vinyl pyrrolidone), poly(methyl methacrylate), poly (vinyl alcohol), poly(acrylic acid), polyacrylamide, poly(ethylene-co-vinyl acetate), poly(ethylene glycol), poly(methacrylic acid), polyactides (PLA), polyglycolides (PGA), poly(lactide-co-glycolides) (PLGA), polyanhydrides and polyorthoesters, and, wherein the substance comprises a therapeutic substance, a cosmetic substance or a combination thereof.

2. The composition of claim 1, wherein the therapeutic substance is selected from the group consisting of anesthetics, hypnotics, sedatives, sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmondics, appetite suppressants, neuroactive substances, neurotransmitter agonists, antagonists, receptor blockers, reuptake modulators, beta-adrenergic blockers, calcium channel blockers, disulfarim, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists, hormone antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, anti-inflammatories, wound care products, antithrombogenic agents, antitumoral agents, antithrombogenic agents, antiangiogenic agents, antigenic agents, wound healing agents, plant extracts, growth factors, growth hormones, cytokines, immunoglobulins, osteoblasts, myoblasts, neuroblasts, fibroblasts, glioblasts; germ cells, hepatocytes, chondrocytes, keratinocytes, smooth muscle cells, cardiac muscle cells, connective tissue cells, epithelial cells, endothelial cells, hormone-secreting cells, neurons, emollients, humectants, anti-rejection drugs, spermicides, conditioners, antibacterial agents, antifungal agents, antiviral agents, antibiotics, tranquilizers, cholesterol-reducing drugs, antitussives, histamine-blocking drugs and monoamine oxidase inhibitor.

3. The composition of claim 1, wherein the electroprocessed material is crosslinked.

4. A composition comprising an electroprocessed material, wherein the electroprocessed material is made by a process comprising the step of simultaneously electroprocessing a solution comprising a natural polymer that is an extracellular matrix protein or polymerized thrombin and two or more synthetic polymers, wherein the synthetic polymers are selected from the group consisting of poly (urethanes), poly(siloxanes), silicones, poly(ethylene), poly (vinyl pyrrolidone), poly(2-hydroxy ethyl methacrylate), poly(N-vinyl pyrrolidone), poly(methyl methacrylate), poly (vinyl alcohol), poly(acrylic acid), polyacrylamide, poly (ethylene-co-vinyl acetate), poly(ethylene glycol), poly (methacrylic acid), polylactides (PLA), polyplycolides (PGA), poly(lactide-co-glycolides) (PLGA), polyanhydrides and polyorthoesters.

5. The composition of claim 4, wherein the extracellular matrix protein is selected from the group consisting of collagen, fibrin, fibrinogen, elastin, laminin and fibronectin.

6. The composition of claim 5, wherein the electroprocessed material comprises collagen and two or more polymers, and wherein the electroprocessed collagen comprises a repeated longitudinal banding pattern, wherein the repeated longitudinal banding pattern occurs at a spacing of about 65 nm to 67 nm.

7. The composition of claim 5, wherein the electroprocessed material comprises one or more collagen types and two or more polymers.

8. The composition of claim 4, further comprising one or more molecules, cells, objects or combinations thereof.

9. The composition of claim 4, further comprising a therapeutic substance, a cosmetic substance or a combination thereof.

10. The composition of claim 9, wherein the therapeutic substance is selected from the group consisting of anesthetics, hypnotics, sedatives, sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmondics, appetite suppressants, neuroactive substances, neurotransmitter agonists, antagonists, receptor blockers, reuptake modulators, beta-adrenergic blockers, calcium channel blockers, disulfarim, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists, hormone antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, anti-inflammatories, wound care products, antithrombogenic agents, antitumoral agents, antithrombogenic agents, antiangiogenic agents, antigenic agents, wound healing agents, plant extracts, growth factors, growth hormones, cytokines, immunoglobulins, osteoblasts, myoblasts, neuroblasts, fibroblasts, glioblasts; germ cells, hepatocytes, chondrocytes, keratinocytes, smooth muscle cells, cardiac muscle cells, connective tissue cells, epithelial cells, endothelial cells, hormone-secreting cells, neurons, emollients, humectants, anti-rejection drugs, spermicides, conditioners, antibacterial agents, antifungal agents, antiviral agents, antibiotics, tranquilizers, cholesterol-reducing drugs, antitussives, histamine-blocking drugs and monoamine oxidase inhibitor.

11. A composition comprising:
an electroprocessed material, wherein the electroprocessed material is made by a process comprising the step of simultaneously electroprocessing from a solution a natural polymer that is an extracellular matrix protein or polymerized thrombin and two or more synthetic polymers, wherein the synthetic polymers are selected from the group consisting of poly(urethanes), poly(siloxanes), silicones, poly(ethylene), poly(vinyl pyrrolidone), poly(2-hydroxy ethyl methacrylate), poly (N-vinyl pyrrolidone), poly(methyl methacrylate), poly (vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides and polyorthoesters, and wherein the electroprocessing is selected from the group consisting of electrospraying, electrosputtering, electrospinning or electroaerosol treatment of the solution.

12. The composition of claim 11, further comprising a substance, wherein the substance comprises a therapeutic substance, a cosmetic substance or a combination thereof.

13. The composition of claim 12, wherein the substance is selected from the group consisting of hormones, growth factors, growth hormones, cytokines, immunoglobulins, osteoblasts, keratinocytes, cardiac muscle cells, hormone-secreting cells, antibacterial agents and antibiotics.

14. The composition of claim 1, wherein the substance is selected from the group consisting of hormones, growth factors, growth hormones, cytokines, immunoglobulins, osteoblasts, keratinocytes, cardiac muscle cells, hormone-secreting cells, antibacterial agents and antibiotics.

15. The composition of claim 1, wherein the extracellular matrix protein comprises collagen.

16. The composition of claim 4, wherein the extracellular matrix protein comprises collagen.

17. The composition of claim 11, wherein the extracellular matrix protein comprises collagen.

18. The composition of claim 1, wherein the extracellular matrix protein is selected from the group consisting of collagen, fibrin, fibrinogen, elastin, laminin and fibronectin.

19. The composition of claim 1, further comprising one or more molecules, cells, objects or combinations thereof.

* * * * *